United States Patent
Seong et al.

(10) Patent No.: US 9,556,242 B2
(45) Date of Patent: Jan. 31, 2017

(54) METHOD FOR REGULATING CIRCADIAN RHYTHMS

(75) Inventors: Jae-Young Seong, Seoul (KR); Jong-Ik Hwang, Seoul (KR); Hyun Kim, Seoul (KR); Dong-Gyu Kim, Seoul (KR); Se-Hyung Cho, Seoul (KR); Gi-Hoon Son, Seoul (KR); Kyung-Jin Kim, Seoul (KR)

(73) Assignee: ANYGEN CO., LTD., Jeollanam-do (KR)

( * ) Notice: Subject to any disclaimer, the term of this patent is extended or adjusted under 35 U.S.C. 154(b) by 0 days.

(21) Appl. No.: 13/981,592

(22) PCT Filed: Jan. 20, 2012

(86) PCT No.: PCT/KR2012/000536
§ 371 (c)(1),
(2), (4) Date: Sep. 10, 2013

(87) PCT Pub. No.: WO2012/102529
PCT Pub. Date: Aug. 2, 2012

(65) Prior Publication Data
US 2013/0345141 A1 Dec. 26, 2013

(30) Foreign Application Priority Data
Jan. 24, 2011 (KR) .................. 10-2011-0007064

(51) Int. Cl.
*C07K 14/435* (2006.01)
*C12Q 1/68* (2006.01)
*G01N 33/68* (2006.01)
*C07K 7/08* (2006.01)
*A61K 38/10* (2006.01)

(52) U.S. Cl.
CPC .............. *C07K 14/435* (2013.01); *A61K 38/10* (2013.01); *C07K 7/08* (2013.01); *C12Q 1/6883* (2013.01); *G01N 33/6896* (2013.01); *G01N 2800/2864* (2013.01)

(58) Field of Classification Search
CPC ......... A61K 38/10; C07K 7/08; C07K 14/435; C12Q 1/6883; G01N 33/6896; G01N 2800/2864
See application file for complete search history.

(56) References Cited

U.S. PATENT DOCUMENTS

| | | | |
|---|---|---|---|
| 2005/0221359 A1* | 10/2005 | Hsueh et al. | .................. 435/6 |
| 2006/0140974 A1 | 6/2006 | Choe et al. | |
| 2008/0124335 A1 | 5/2008 | Kangawa et al. | |
| 2008/0318871 A1 | 12/2008 | Khan et al. | |
| 2009/0142793 A1 | 6/2009 | Kay et al. | |

OTHER PUBLICATIONS

Terasaki et al., J. Drug Targeting, vol. 8, 2000, pp. 353-355.*
Toll et al. Peptides derived from the prohormone proNPQ/spexin are potent central modulators of cardiovascular and renal function and nociception. FASEB J. Feb. 2012;26(2):947-54. Epub Oct. 28, 2011.*
Seo et al. The circadian rhythms of blood pressure and heart rate in the hypertensive subjects: dippers and non-dippers. Yonsei Med J. Jun. 2002;43(3):320-8.*
International Search Report for PCT/KR2012/000536.
Ikeda et al., "Bmal1 Is an Essential Regulator for Circadian Cytosolic Ca2+ Rhythms in Suprachiasmatic Nucleus Neurons", The Journal of Neuroscience, vol. 34, No. 36, pp. 12029-12038, (2014).
O'Neill et al., "cAMP-Dependent Signaling as a Core Component of the Mammalian Circadian Pacemaker", Science, vol. 320, pp. 949-953, (2008).

* cited by examiner

*Primary Examiner* — Gregory S Emch
(74) *Attorney, Agent, or Firm* — Vorys, Sater, Seymour & Pease LLP; Mih Suhn Koh

(57) ABSTRACT

The present invention relates to a composition for regulating circadian rhythms, a composition for diagnosing circadian rhythm disorders and a diagnostic kit, wherein the composition for regulating circadian rhythms comprises NQ peptides, C12orf39 genes, NQ peptides cDNA and the like, which relate to circadian regulation in vertebrates as main components.

7 Claims, 16 Drawing Sheets

Fig. 3

| | |
|---|---|
| Human | NWTPQAMLYLKGAQ-NH$_2$ |
| mouse | NWTPQAMLYLKGAQ-NH$_2$ |
| Rat | NWTPQAMLYLKGAQGH |
| Zebrafish-1 | NWTPQAMLYLKGTQ-NH$_2$ |
| Zebrafish-2 | NWGPQSMLYLK-NH$_2$ |
| Fugu-1 | NWTPQAMLYLKGTQ-NH$_2$ |
| Fugu-2 | NWSPQSMLYLKGA |
| Xenopus-1 | NWGPQSMMYLKGKH-NH$_2$ |
| Xenopus-2 | NWGPQSMMYLK-NH$_2$ |

SEQUENCE LISTING

<160> NUMBER OF SEQ ID NOS: 10

<210> SEQ ID NO 1
<211> LENGTH: 15
<212> TYPE: PRT
<213> ORGANISM: Artificial Sequence
<220> FEATURE:
<223> OTHER INFORMATION: NQ Peptide 1

<400> SEQUENCE: 1

Asn Trp Thr Pro Gln Ala Met Leu Tyr Leu Lys Gly Ala Gln Gly
1               5                   10                  15

<210> SEQ ID NO 2
<211> LENGTH: 14
<212> TYPE: PRT
<213> ORGANISM: Artificial Sequence
<220> FEATURE:
<223> OTHER INFORMATION: NQ Peptide 2

<400> SEQUENCE: 2

Asn Trp Thr Pro Gln Ala Met Leu Tyr Leu Lys Gly Ala Gln
1               5                   10

<210> SEQ ID NO 3
<211> LENGTH: 16
<212> TYPE: PRT
<213> ORGANISM: Artificial Sequence
<220> FEATURE:
<223> OTHER INFORMATION: NQ Peptide 3

<400> SEQUENCE: 3

Asn Trp Thr Pro Gln Ala Met Leu Tyr Leu Lys Gly Ala Gln Gly His
1               5                   10                  15

<210> SEQ ID NO 4
<211> LENGTH: 7490
<212> TYPE: DNA
<213> ORGANISM: Artificial Sequence
<220> FEATURE:
<223> OTHER INFORMATION: C12orf39

<400> SEQUENCE: 4
taaaataacc cagcactgcc ctgtcatgtc atcttggctg cctttactta ctaacctaag      60
catggtgcca gtagcgtaga gagagtcctc ccctaactaa aagattagct tgagaccaag     120
aggtaggagg tagccattca acacatattt gttaaatcac tgactagatg gacacttgag     180
tagatgaatg actggtgtca agttcctctg aggctcgcta accttttggt gttcacaggg     240
gtgattcatc tccgcccaca gttacatttg tttcattcat aatggtgaaa tgcattgggc     300
agctaacagg aaaaacaaag gtgacggtgc tgatacagtc agaatgtctc ctggctggtg     360
tggtcagttc ccaaacaaat gatatccgct catcaatcat tgtcctattt ctgccaatta     420
gacctcccca gaggagtcat caggtccgct cagttctgaa gattgacaag ctaccctcgt     480
ggtctcctct cctctgtgca gactccaaca ctaggagttt ttaaagcccg ggggttgtaa     540
caagtttaga agactggaag gtagggcgag agattgtggg gctctggaca gggtcggaac     600
atgaaggtaa gcagcagatg tgtgcacccg atatctttcc agctgttcta taaactgtct     660
acctttctat ctaggttata tgtactgagc attgtagtga ctggacattt gaagaatagt     720
gcctttaaat agtgcaacct gattttgctg aatagaactt atccaccaat tctttatttg     780
ggtgaagtta tgaaaatcat atctttctaa tttttaaagt tactctttat ggattaacta     840

| | |
|---|---|
| gaaggtggga tcatatactg agtgaagtaa ggggcctact gtcctctctg aagaggaagc | 900 |
| aaaacgaaaa caaacaaaca aaaacaaac aaaaaaacaa atgcagccac actccgtccg | 960 |
| atgaggctgt gtttggtcga tgtgtcttgt aggggcccag cgtcctggca gtgacagccg | 1020 |
| tggtccttct cctggtgctg tctgcgctgg aaaactccag cggtgctcca caggtaatgc | 1080 |
| agagaacaca aaccccgggt tcggactagg cagcctctgt ttttgctttt tccacccgct | 1140 |
| gcattgtaat aacgattctt ctctcctccc tgcactgcag cgactctctg agaagaggaa | 1200 |
| ctggactccc caagctatgc tctatctgaa gggtgcacgt gagttccata ctccttattc | 1260 |
| tcctcacgga gggtgatggg agacatccgg ggactcctaa gagacagggt cacagccggc | 1320 |
| tccagtaaat aattaggatt tcagacaatc cagaaaccat aggagtgggc aggtgggaca | 1380 |
| aaaatactct gatggccaga aaccctcccc caaagaggtg tttggggtca ctactgtgac | 1440 |
| ctggcactct cgaagctgag gcaggagaaa tgctagcttg gctacctag tgggctccag | 1500 |
| gtcaaactaa gatcctgtca gggaaaaaag gaaaaggag gagggaggaa ataagaaaga | 1560 |
| gctggagaag ggttcaagaa aggcgaaata aggaaaggg gggaggaaa agtgggggat | 1620 |
| aagaaggaag gagaggaggg agaaggggag ggaatgaagg aaagctggct gattgaattt | 1680 |
| agagaactaa tgattgaaca aagaaggtgc ctggtagagg agcatagaat ggcaaaagaa | 1740 |
| gttaggaagg gagagaggaa gggaagggggt ggaaggaaag agagaggcac gcgcgaatcc | 1800 |
| cactggggct gctctccgaa tcgaggtcgc atccctggcg ggaacccgcg atctccctga | 1860 |
| tcctggggtc tagctgtctg cctcagtcct cctcgtgtcc cacccctccc ccttcccacc | 1920 |
| ccccgcagag ggccgccgct tcctctccga ccagagccgt aggaaggagc ttgcagaccg | 1980 |
| gccgcctcca ggtgagcgag cgctgcgcct atggcggggt tccacctgcc ctgtccccta | 2040 |
| gcaggcggct agtgagcccg ggtccccaaa ctggcagggt ctgtagcaca gacacagggc | 2100 |
| agagagaagc cccctctccg ggtatttctg gaaagagcct tgatctttct cttcctaaat | 2160 |
| agcaattgct actaaataat cacttagaca tttcaagtat atctttctcc taaatgatta | 2220 |
| gaaacagccg ccaaaggttt ttaaccaaac gcaattaagt taaaagctat gaacgaatga | 2280 |
| ttgagccagg tatgaatgac tgagaggagg atcagttttc ttccgggaca aactctagat | 2340 |
| aagctatcca atctcaagtc ctcagcccta aatagttgta ggaaacgcgg gggggggggg | 2400 |
| gaatcataaa ttacagagga tgcataagac gagttggggg acagagagag ggtggaaact | 2460 |
| atgcaaacag tactcatcat gtatgaaatt ctccaaaaaa caaattaatt aagaaatagg | 2520 |
| ttcaggaaca ttttttttcc ttgatgaact taatgacatt gcagtttaaa cagaagaaaa | 2580 |
| aataatcttg gtaaaatttt gtatagaagt accaagaata aaagctatac ttacttggag | 2640 |
| agatattcag cactgcttag catgccgata gcagatgctt tcagcttttg tttcagttcc | 2700 |
| tgagtttgca gtgtgactgg tcttgttttt tagggtagaa tatgtttctt ctcttcctgc | 2760 |
| tacttccgat taaaactccc agcctgtcct agatcaggac catgtcatct gtcaacttaa | 2820 |
| gtatgaaata gactgcagcg gcatatccct gtgacccagt aaacatataa ttcaataaaa | 2880 |
| gtgaaataac tctgactatt tagccagggt ctcttcattc aaatagctaa ttacctccta | 2940 |
| tgtgaccacg attgtaatcg gttatctcaa attgacttgg aagggggaaa cagggagat | 3000 |
| ccggctccaa tgagatattt tggccaaaac aaccttcttt aagctgtgag aaggaaaatg | 3060 |
| cacccccttc taaaccctgg cgagagaaag ctgtgtggcc tcctactcat cttccttttg | 3120 |
| ctacatactc catactccct agcattcatc ctcaggtata aacaaatgga aggtcactgt | 3180 |
| ggtggcagca agattgatca tcaggcaaag gcaccggcca ccaaacctga ctccctaagt | 3240 |

```
tcaatccata ggacccacat atgaaaggag agtcacacac atgcacacac acacacacac    3300
acacacgaat gcactaaata aaatgcaata taaatgttta ataaactttt ttttaaaaaa    3360
aatcagcaca tagtatacag agttttttct agtcttgtat ggcagagtaa gattcatgta    3420
catgggtgtt tagttgacac aaatatctga atgctgatct gtttacgatg ttaatgggca    3480
ggaatgtgtg aatgcttctt tctttatatg aatatcaagg ctgagctcat ttctgtttct    3540
ccagaaagac gaaacccaga tcttgaactg ctgactctcc cagaggctgc agccctgttt    3600
ctggcttcct tggaaaaatc acaaaaggt gcaggtgtgg tggcttctct gtattctggg     3660
ctgagaacct ttgtgtcctg actgctccct ccccaaaccc acagaaacac ttattcaata    3720
aaggccagtt acttcccagt aaaatgagtc ccaagaatac taaagcacta ccttgatgag    3780
agtggggaaa gaaccgtagc ctattgttag tgatgtttgt ttgtttgttt gttttgaata    3840
taatgcctat gtattccaag ctggcttcaa attccttatg tagcaaaggc tggccttgaa    3900
catcttattg ccctgcctcc accaaatagg actttttaaaa cttttaaagc tccaattggc    3960
ttcattgttt tataactaaa aacagcaaag ccaaaaatac gaaataatca aaatccaatt    4020
gctcaccatt caaaactaaa ccaaatgaaa gttcttattg ccaatccttt ttccctttcc    4080
cacacagcag tagatgtggt tcccctaac agacaggagc agccttgact acaggcctgg     4140 ttttttttcac ctttctgccc agcttctaag ccaggagtgg atgtaatctt caaacagcca   4200
ttctatccct gagatttaga agtaccaaga caattaaggc atcttggcaa tggatcagct    4260
gggtctttgg aacttcatag acctcagtat aaatccatgc cacactgagt gaggctgtca    4320
ggggataaat tttgagtctg ttttctcctt ccaccatgat ggttccagga actgaagttg    4380
ggttgttaga cttgagagca ggggcccatc cctgctgtgc cttctcactg gctctaatgg    4440
ttggcatgtt ctgggtagct tgtctctgga gatgcgccaa agaaattgct tcttttttatt   4500 attattatct ttattttatt tatttatata ttatataatt tattattatt atcttattat    4560
atgttttatt atcctaaatg aagggaggag ttgtgggttc ccatatcata tgtcaatcat    4620
tttctctaat attttcattg cagaatctct aggtttcata tggatgtctc ttacatcatg    4680
aacttaaatt ccaatggagt ttgtactggg atgttttttct gtcccacctc tacccttag    4740 gcgtgtatgt gtctgtgttt ccgtccgtgt gcccacattt tctttccctc tagagagaag    4800
cacgttttct aattactatt tttcaaagaa tgtgagcaat gggataggt caggattcaa      4860 attatattgt gagtagctga gagaacgttg ctttatctag aaggcagtcg ttggaaaatt    4920
aaaatctagg gcatgtatgc tgtgtcagcc actgttctct accccactca ggtttcatct    4980
cttgtacctt tatatttagg gtcctgtgat cttgttacta tgtaatcttt atgagatgca    5040
ccaggcctaa catttttgta tttgcaccca gctaacaagt gtgtttgcct ttggtctcag    5100
tggttaccca gaagaaatca cccgatgaag gaatatcttc aagtgtgtcc ctgtgtcatc    5160
tttcccatga gggagctata tcatcaggaa tcacgggcca catcattttg atgcaaatga    5220
atggttataa tgtcaggtgc ttagactaga ggcatgttaa tcagagcaag acagtctcta    5280
tatacttctg ccaaacttgc cacatcacac ttaattttatt gtagagattt ggatgttggg    5340
agctagaatg tagctcagtt ggtagagtgt ttgcccagca agcacaaggc cttgggctc     5400 aacccctagt actatgtaaa gaagcatggt agtgaatgcc tgtgatcccg ggagctggga    5460
agtggaggca ggaagatcag aagttcaagg tcacagctac atacattctg gatttaaaaa    5520
aaaaatgtga attgccagcc atgattgagt tagttgttgg tagcattggc catgattgag    5580
```

|  |  |
|---|---|
| aactaaaatg tctatttcct gaggttctgt ttcccctct aaagccatga ctgtgtgttc | 5640 |
| acaagaaaag gtgttttctt tttttcttac agatgaagga gggaattttg ataaaagcga | 5700 |
| actcttggaa gacagactct tcaactggtg aaaacacacc aggacacctt caagtgtagt | 5760 |
| cctcgttgtg atggaaacca gaaccacacg aggggcccgt gcacccttcc ttccacccga | 5820 |
| gaaacctgca cctctaggtt tagtcccatg gaaatcctgg ctggaacatt accactggct | 5880 |
| ggaacatcac cattggctgg aacatcaccc atgtcttacg taggcttgga ttattcaggg | 5940 |
| cctttcacgt gtcaaggctg agaactcaga aatgttcttt cttctccctg cagtcaggcc | 6000 |
| ctgctttgat tttggccgtt tgttttctta tcccataatt cccttgcctt tggtgccact | 6060 |
| cagaagcaaa tatcgctgtc cctcatcgtc ccagccccag tgagagagag ggtgcaccgg | 6120 |
| gaagggaatg gataggatct cctagatagg aactcgtctg cgaggtcaaa taaggaggga | 6180 |
| ggcaaggaga agatgcctga taaagctccc atgaaaacac atctctgtcg ctgctgaaac | 6240 |
| agggcaccat ccatgatgct gaaactgctg aaggtctgt gaaaactgag gaccgggagc | 6300 |
| ctctttgtgc tcctaggacc taactgaact ccacatagaa gcttagacct taaggttact | 6360 |
| gacacacaaa cagatggtga tgtcagagtt tgctggagca cacggcacac aaaggtacaa | 6420 |
| accagttgtt caggttcaga ggtagtccat cttctgtgac tttgcattaa ggtattccca | 6480 |
| tgacacaagt gagtgccaca tgcatgattt accctttccc atgcacacac atgcacaggc | 6540 |
| acatgcacac gcacacagtg aaggaatttg ggagtgaaat ccctatacca aggagactaa | 6600 |
| cttatttgga attacatctt gatcaccgtg tgtgtgtgtg tgtgtatgtg tgtgtgtgtg | 6660 |
| tgtgtgtgtt taaaaaaata ttcaattcag agtcattaac cataagtgct caagtgacaa | 6720 |
| agtagcgata cttattgtcc ccagcttaca gttattacct tgaactatac agtatcttta | 6780 |
| tgtaaatacc gctgtaatct gatattttaa ctcaactgtg ttaaatcaaa acctagtgta | 6840 |
| tatgttttgc ctgcttctca gttcataaat aaacaataaa actatattct agttaatgta | 6900 |
| ccattggctt ccatcaaaaa tattcaaact ctaaatagat gcttgtcact tgtcaagact | 6960 |
| tgacattgac gtggacttac aagagaatcc catatccagt gtatggagta actgatgggg | 7020 |
| acacactggc atatattgct cattttaaaa gtcctttatt ccaaggctgt ttttaacacc | 7080 |
| tagctcacaa agtagttttt ctcatagctg ccccacatag tctccagtgt ttcatgctgt | 7140 |
| aatgtagctt cttaaaatct atctaaataa gagtagctgt tcaagtaaca ccctcctctt | 7200 |
| catcacctcc cttaaatgct ctgcagtaca ggcgtgctgg ttaattagat ggctccctct | 7260 |
| ctccagtttg ataaaacttc tcaaccctcc taggatgtgc ctttgttagg ttttccttgc | 7320 |
| tatagcaagt tacccgagac ttgggaattt atcatgaaaa aaataggtct attttgattc | 7380 |
| ggggtttgga aggctgtgag atccaagaac atgtttctgg catctttcta gtgttttgaa | 7440 |
| gaacctaatg ctgctcacaa cctgagagaa aagtagatga taagagaatc | 7490 |

<210> SEQ ID NO 5
<211> LENGTH: 14
<212> TYPE: PRT
<213> ORGANISM: Artificial Sequence
<220> FEATURE:
<223> OTHER INFORMATION: anti-NQ peptide epitope 1

<400> SEQUENCE: 5

Asn Trp Thr Pro Gln Ala Met Leu Tyr Leu Tyr Gly Ala Gln
1               5                   10

<210> SEQ ID NO 6

```
<211> LENGTH: 24
<212> TYPE: PRT
<213> ORGANISM: Artificial Sequence
<220> FEATURE:
<223> OTHER INFORMATION: anti-NQ peptide epitope 2

<400> SEQUENCE: 6

Ser Leu Glu Lys Ser Gln Lys Gly Ala Asp Glu Gly Gly Asn Phe Asp
1               5                   10                  15

Lys Ser Glu Leu Leu Glu Asp Arg
            20

<210> SEQ ID NO 7
<211> LENGTH: 21
<212> TYPE: DNA
<213> ORGANISM: Artificial Sequence
<220> FEATURE:
<223> OTHER INFORMATION: NQ peptide RT PCR primer 1

<400> SEQUENCE: 7
cgactctctg agaagaggaa c                                          21

<210> SEQ ID NO 8
<211> LENGTH: 17
<212> TYPE: DNA
<213> ORGANISM: Artificial Sequence
<220> FEATURE:
<223> OTHER INFORMATION: NQ peptide RT PCR primer 2

<400> SEQUENCE: 8
tctcagcctt gacacgt                                               17

<210> SEQ ID NO 9
<211> LENGTH: 357
<212> TYPE: DNA
<213> ORGANISM: Artificial Sequence
<220> FEATURE:
<223> OTHER INFORMATION: NQ peptide cDNA

<400> SEQUENCE: 9 atgaagggc  ccagcgtcct  ggcagtgaca  gccgtggtcc  ttctcctggt  gctgtctgcg      60
ctggaaaact  ccagcggtgc  tccacagcga  ctctctgaga  gaggaactg   gactccccaa    120 gctatgctct  atctgaaggg  tgcacagggc  cgccgcttcc  tctccgacca  gagccgtagg    180
aaggagcttg  cagaccggcc  gcctccagaa  agacgaaacc  cagatcttga  actgctgact    240
ctcccagagg  ctgcagccct  gtttctggct  tccttggaaa  aatcacaaaa  aggtgcagat    300
gaaggaggga  attttgataa  aagcgaactc  ttggaagaca  gactcttcaa  ctggtga       357

<210> SEQ ID NO 10
<211> LENGTH: 116
<212> TYPE: PRT
<213> ORGANISM: Artificial Sequence
<220> FEATURE:
<223> OTHER INFORMATION: C12orf39 Protein

<400> SEQUENCE: 10

Met Lys Gly Leu Arg Ser Leu Ala Ala Thr Thr Leu Ala Leu Phe Leu
1               5                   10                  15

Val Phe Val Phe Leu Gly Asn Ser Ser Cys Ala Pro Gln Arg Leu Leu
            20                  25                  30

Glu Arg Arg Asn Trp Thr Pro Gln Ala Met Leu Tyr Leu Lys Gly Ala
        35                  40                  45
```

-continued

```
Gln Gly Arg Arg Phe Ile Ser Asp Gln Ser Arg Arg Lys Asp Leu Ser
    50              55                  60

Asp Arg Pro Leu Pro Glu Arg Arg Ser Pro Asn Pro Gln Leu Leu Thr
 65          70              75                      80

Ile Pro Glu Ala Ala Thr Ile Leu Leu Ala Ser Leu Gln Lys Ser Pro
             85              90                  95

Glu Asp Glu Glu Lys Asn Phe Asp Gln Thr Arg Phe Leu Glu Asp Ser
            100             105                 110

Leu Leu Asn Trp
        115
```

METHOD FOR REGULATING CIRCADIAN RHYTHMS

CROSS REFERENCE TO RELATED APPLICATIONS AND CLAIM OF PRIORITY

This patent application is a National Phase application under 35 U.S.C. §371 of International Application No. PCT/KR2012/000536, filed Jan. 20, 2012, which claims priority to Korean Patent Application No. 10-2011-0007064 filed Jan. 24, 2011, entire contents of which are incorporated herein by reference.

FIELD OF THE INVENTION

The present invention relates to a composition for regulating circadian rhythm, a composition and a kit for diagnosing a circadian rhythm disorder, including the NQ peptide, the C12orf39 gene and cDNA of the NQ peptide relate to circadian regulation in vertebrates as main ingredients.

DESCRIPTION OF THE RELATED ART

In adaptation to the daily light/dark cycles by the earth's magnetic field, all organisms have developed by persistently, repetitively and periodically external environments.

On the other hand, since several external cues including light, temperature, humidity, vibration and sound are key elements which may synchronize an endogenous internal clock (biological clock) with external environments, Zeitgeber (Zeitgebers, zeit=time, gebers=giver) has established in a concept regardless of the meaning such as the artificially or naturally occurring [Aschoff J, Handbook of Behavioral Neurobiology. New York, Plenum Press, 1981].

In addition, under condition of eliminating Zeitgeber, the biological clock actually shows rhythmicity of free-running with the period of circa dies [Sharma and Chandrashekaran, Current Science, 2005]. Because the endogenous biological clock induces optimal responses to prepare for the foreseeable future such that hosts may give themselves advantages of selective or survival [Plamen D. Penev et al, Am. J. Physiol. Heart. Circ. Physiol., 1998; Diego A Golombek and Ruth E. Rosenstein, Physiol. Rev., 2010].

Meanwhile, the synchronizing mechanism of the biological clock by the light is described with an anatomical, molecular and signaling pathway models.

In photic cue, an eye of organism is its receptor. The translated electrical signals pass through retino-hypothalamic tract (RHT) and optic chiasm (OX), and transmit to suprachiasmatic nucleus (SCN) situated in anterior hypothalamic area [David M. Berson et al., Science, 2002].

SCN is divided into a core part and a shell part. Central pacemaker neurons are in charge of regulating the internal rhythmicity within organisms to adjust for outside through the interaction with the received signals from SCN [Ralph M R et al., Science, 1990].

In this time-keeping system, where a first initiator is external information such as the light, bmal1 and clock genes present in SCN are key genes which synchronize endogenous biological clock within organisms with external information. After expression, the genes form heterodimer, of which bind to an E-box as promoter of clock-related genes such as Per, Cry, Ppar, Ror, Rev-Erb to activate the gene expression.

On the other hand, the expressed clock-related genes have negative-feedback loop which leads to no longer autoregulatory transcription by inversely inhibiting the transcription of bmal1 or heterodimerization of CLOCK:BMAL1 [Wangjie Yu, Biochem. Biophys. Res. Commun., 2002].

SCN has complicated networks by various types of cells consisting of amino acid/amine nerves including a variety of peptidergic neuron and astrocytes which support them or perform their own independent function. Vasoactive intestinal polypeptide (VIP), Arginine-vasopressin (AVP), γ-aminobutyric acid (GABA), Pituitary adenylate cyclase-activating polypeptide (PACAP), 5-HT (Serotonin), Glutamate, Neuropeptide Y (NPY) and Gastrinreleasing peptide (GRP) have been known as neuropeptides or neurotransmitters secreted from SCN [Watts and Swanson, J. Comp. Neurol., 1987].

These bioactive peptides have been known to serve as necessary functions in eating, reset and homeostasis maintenance which are important in circadian rhythm. Interestingly, cerebellin-1, neuroendocrine protein 7B2, proenkephalin B, secretogranin 1, secretogranin 3, tachykinin 3, acyl-CoA-binding protein, brain-specific polypeptide PEP-19 and PEBP-1 as endogenous neuropeptides present in SCN have been currently found to novel substances to be related with circadian regulation through LC-FTMS/MS analysis [Lee et al., Mol. Cell. Proteomics, 2010].

These results strongly suggest possibility that novel neuropeptides which are unknown functions related to circadian regulation are still exist in vivo.

Human genome project launched in 1990 have been contributed to develop numerous genes actually encoding proteins in humans [National human genome institute].

In 2005, most a vast amount of genome-database from unicellular species (*Schizosaccharomycespombe, Saccharomycescerevisiae*), plants (*Arabidopsisthaliana, Oryzasativa*), insects (*Drosophila melanogaster; Anophelesgambiae*), nemathelminthes (*Caenorhabditis elegans, Caenorhabdilisbriggsae*), chordates (*Cionaintestinalis, Cionasavignyi*), teleostei (*Takifugurubripes, Danio rerio*) to mice (*Mus musculus*) has been established [Robert Fredriksson, Mol. Pharmacol., 2005].

As a result, homologous genes encoding same proteins between different species could be found and amino acid sequences of these proteins could be compared/analyzed, whereby the biological importance of certain amino acids evolutionarily conserved is able to be predicted. Besides, biological active portions of novel peptides currently not known are able to be predicted accurately through this analysis.

Throughout this application, various publications and patents are referred and citations are provided in parentheses. The disclosures of these publications and patents in their entities are hereby incorporated by references into this application in order to fully describe this invention and the state of the art to which this invention pertains.

SUMMARY

It is an object of this invention to provide a composition for regulating circadian rhythm.

It is another object of this invention to provide a pharmaceutical composition for preventing or treating a circadian rhythm disorder.

It is still another object of this invention to provide a composition for diagnosing a circadian rhythm disorder.

It is further object of this invention to provide a method for regulating circadian rhythm.

It is still further object of this invention to provide a method for preventing or treating a circadian rhythm disorder.

It is further object of this invention to provide a method for determining a circadian rhythm disorder.

Other objects and advantages of the present invention will become apparent from the following detailed description together with the appended claims and drawings.

In one aspect of this invention, there is provided a composition for regulating circadian rhythm, comprising: a peptide comprising the amino acid sequence as set forth in SEQ ID NO:1, a peptide comprising the amino acid sequence as set forth in SEQ ID NO:2, a peptide comprising the amino acid sequence as set forth in SEQ ID NO:2 in which the carboxyl group of the glutamine residue at the carboxyl-terminus is modified by an amino group, a peptide comprising the amino acid sequence as set forth in SEQ ID NO:3, the C12orf39 gene comprising the nucleotide sequence as set forth in SEQ ID NO:4, cDNA of the NQ peptide comprising the nucleotide sequence as set forth in by SEQ ID NO:9, or a nucleotide sequence comprising the sequence spanning positions 106-147 or positions 106-150 in cDNA of the NQ peptide as set forth in SEQ ID NO:9.

In another aspect of this invention, there is provided a pharmaceutical composition for preventing or treating a circadian rhythm disorder, comprising: (a) a therapeutically effective amount of a peptide comprising the amino acid sequence as set forth in SEQ ID NO:1, a peptide comprising the amino acid sequence as set forth in SEQ ID NO:2, a peptide comprising the amino acid sequence as set forth in SEQ ID NO:2 in which the carboxyl group of the glutamine residue at the carboxyl-terminus is modified by an amino group, a peptide comprising the amino acid sequence as set forth in SEQ ID NO:3, the C12orf39 gene comprising the nucleotide sequence as set forth in SEQ ID NO:4, cDNA of the NQ peptide comprising the nucleotide sequence as set forth in by SEQ ID NO:9, or a nucleotide sequence comprising the sequence spanning positions 106-147 or positions 106-150 in cDNA of the NQ peptide as set forth in SEQ ID NO:9; and (b) a pharmaceutically acceptable carrier.

In still another aspect of this invention, there is provided a composition for diagnosing a circadian rhythm disorder, comprising: (i) an antibody specifically binding to a peptide comprising the amino acid sequence as set forth in SEQ ID NO:1, a peptide comprising the amino acid sequence as set forth in SEQ ID NO:2, a peptide comprising the amino acid sequence as set forth in SEQ ID NO:2 in which the carboxyl group of the glutamine residue at the carboxyl-terminus is modified by an amino group, or a peptide comprising the amino acid sequence as set forth in SEQ ID NO:3, (ii) an antibody specifically binding to a peptide epitope as set forth in SEQ ID NO:6, (iii) a primer or a probe specifically binding to the C12orf39 gene comprising the nucleotide sequence as set forth in SEQ ID NO:4, or (iv) a primer or a probe specifically binding to cDNA of the NQ peptide comprising the nucleotide sequence as set forth in by SEQ ID NO:9.

In further aspect of this invention, there is provided a method for regulating circadian rhythm comprising: administering to a mammalian subject in need thereof a composition comprising a peptide comprising the amino acid sequence as set forth in SEQ ID NO:1, a peptide comprising the amino acid sequence as set forth in SEQ ID NO:2, a peptide comprising the amino acid sequence as set forth in SEQ ID NO:2 in which the carboxyl group of the glutamine residue at the carboxyl-terminus is modified by an amino group, a peptide comprising the amino acid sequence as set forth in SEQ ID NO:3, the C12orf39 gene comprising the nucleotide sequence as set forth in SEQ ID NO:4, cDNA of the NQ peptide comprising the nucleotide sequence as set forth in by SEQ ID NO:9, or a nucleotide sequence comprising the sequence spanning positions 106-147 or positions 106-150 in cDNA of the NQ peptide as set forth in SEQ ID NO:9.

In still further aspect of this invention, there is provided a method for preventing or treating a circadian rhythm disorder comprising, administering to a mammalian subject in need thereof a pharmaceutical composition comprising: (a) a therapeutically effective amount of a peptide comprising the amino acid sequence as set forth in SEQ ID NO:1, a peptide comprising the amino acid sequence as set forth in SEQ ID NO:2, a peptide comprising the amino acid sequence as set forth in SEQ ID NO:2 in which the carboxyl group of the glutamine residue at the carboxyl-terminus is modified by an amino group, a peptide comprising the amino acid sequence as set forth in SEQ ID NO:3, the C12orf39 gene comprising the nucleotide sequence as set forth in SEQ ID NO:4, cDNA of the NQ peptide comprising the nucleotide sequence as set forth in by SEQ ID NO:9, or a nucleotide sequence comprising the sequence spanning positions 106-147 or positions 106-150 in cDNA of the NQ peptide as set forth in SEQ ID NO:9; and (b) a pharmaceutically acceptable carrier.

In further aspect of this invention, there is provided a method for determining a circadian rhythm disorder, comprising: (a) contacting a biological sample of interest to (i) an antibody specifically binding to a peptide comprising the amino acid sequence as set forth in SEQ ID NO:1, a peptide comprising the amino acid sequence as set forth in SEQ ID NO:2, a peptide comprising the amino acid sequence as set forth in SEQ ID NO:2 in which the carboxyl group of the glutamine residue at the carboxyl-terminus is modified by an amino group, or a peptide comprising the amino acid sequence as set forth in SEQ ID NO:3, (ii) an antibody specifically binding to a peptide epitope as set forth in SEQ ID NO:6, (iii) a primer or a probe specifically binding to the C12orf39 gene comprising the nucleotide sequence as set forth in SEQ ID NO:4, or (iv) a primer or a probe specifically binding to cDNA of the NQ peptide comprising the nucleotide sequence as set forth in by SEQ ID NO:9; and (b) analyzing the occurrence of an antigen-antibody reaction or a hybridization reaction in the resultant of the step (a).

Since the present composition for regulating circadian rhythm according to the present invention may regulate, the present composition may be used for preventing or treating tiredness, jet lag syndrome, seasonal affective disorder, mood disorder and disorder which may be caused by similar circadian rhythm disorder thereof. In addition, the present composition may be used for diagnosing a circadian rhythm disorder. Using these, the present composition may be used as materials for developing novel drugs on the new level.

BRIEF DESCRIPTION OF THE DRAWINGS

FIG. 3 schematically represents that paralogs of the NQ peptide exist in teleostei and amphibian. It shows possibilities that the present peptide is not only evolutionarily conserved, but also differentiated to other function.

DETAILED DESCRIPTION

Figure 1:
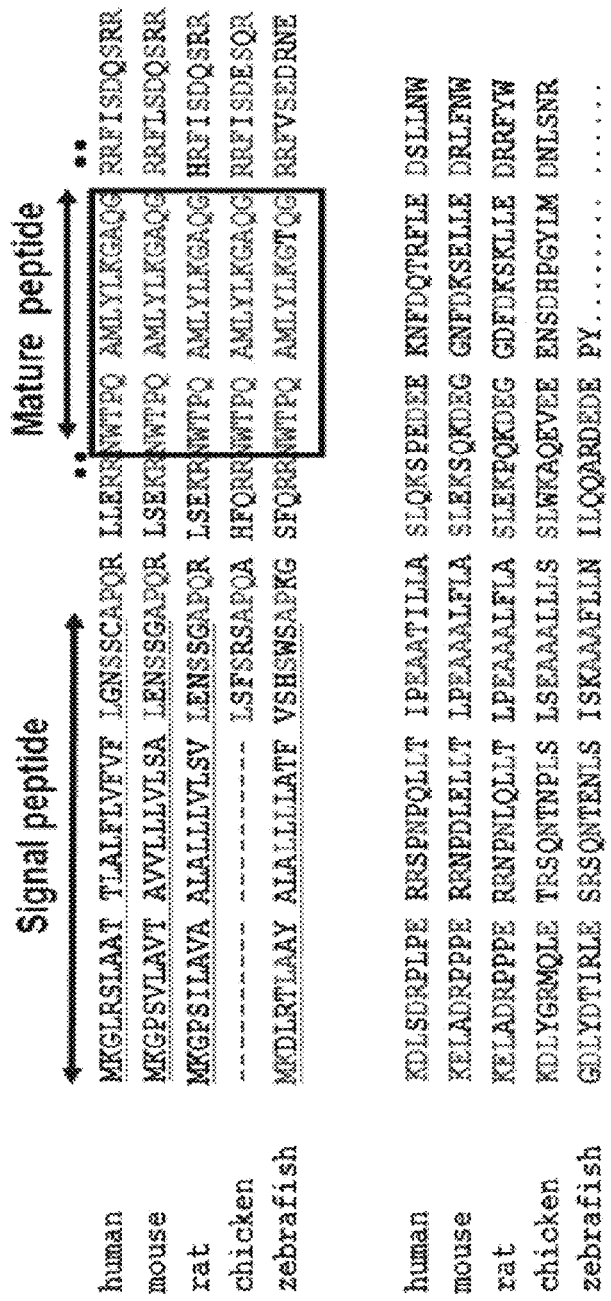
FIG. 1 schematically represents the translated structures after transcription of the C12orf39 gene which has been found in a variety of vertebrates. It means that structures of the mature NQ peptide in the post-translational modification as well as whole amino acid of the NQ peptide were highly conserved between species.

The present invention will now be described in detail as follows.

The present invention provides a composition for regulating circadian rhythm and a pharmaceutical composition for preventing or treating a circadian rhythm disorder. In addition, the present composition may be expressed to "a composition for inducing circadian rhythm phase-shifting effect" or "a composition for normalizing circadian rhythm".

Since the present peptide is a novel peptide, it may be differently called by those ordinarily skilled in the art. Therefore, the present invention is not limited to the name "NQ peptide", and includes all uses related to circadian rhythm using the peptide sequences of SEQ ID NOs:1, 2 and 3, or the gene of SEQ ID NO:4, or the cDNA as set forth in SEQ ID NO:9.

The present invention provide a composition for regulating circadian rhythm including at least one selected from the group consisting of a peptide comprising the amino acid sequence as set forth in SEQ ID NO:1, a peptide comprising the amino acid sequence as set forth in SEQ ID NO:2 in which glutamine residue terminal at the carboxyl-terminus is amino group, the C12orf39 gene as set forth in SEQ ID NO:3, the NQ peptide cDNA as set forth in SEQ ID NO:8.

The present inventors have performed gene screening, and they have found that the present peptide has asparagine (Asn) at the N-terminus and glutamine (Gln) at the carboxyl-terminus. The peptides comprising the amino acid sequence as set forth in SEQ ID NOs:1, 2 and 3 according to the present invention are called "NQ peptide" by the present inventors.

In the peptide of SEQ ID NO:1, glycine (Gly) at the C-terminus is cleaved by α-amidation due to peptidylglycine alpha-hydroxylating monooxygenase (PHM), whereby the glutamine (Gln) terminus has $NH_2$ [Betty A. Eipper and Richard E. Mains, Ann. Rev. Physiol., 1988].

Therefore, the second NQ peptide has the amino acid sequence of SEQ ID NO:2 and the carboxyl group of glutamine at the carboxyl-terminus has $NH_2$.

As a result, they are not attacked by aminopeptidase or synthetase in vivo, contributing to increase in the activity of the present peptide.

Since a histidine residue following the glutamine residue at the carboxyl-terminus also induces activities of the NQ peptide (FIG. 15), the peptide sequences with additionally incorporated glycine and histidine residues into SEQ ID NO:1 are covered by the NQ peptide, corresponding to the NQ peptide form expected to be expressed in rats.

Peptides comprising the amino acid sequence as set forth in SEQ ID NOs:1 to 3 are derived from the C12orf39 gene as set forth in SEQ ID NO:4.

The present inventors have performed genetic screening of composition for regulating circadian rhythm through bioinformatic approach model. Among open reading frames (ORF) of approximately 50,000 types of human genome genes, approximately 2,000 types of genes (secretome) with the potential to be secreted from the cells were selected. As a result, 40 types of genes encoding novel peptides that their functions have not been yet known were researched, and the C12orf39 was developed as a gene encoding composition for regulating circadian rhythm.

Amino acids of the precursors of the present composition expressed from the C12orf39 gene include the amino acid sequence of the mature NQ peptide including signal peptides. The amino acid sequence encoding the peptide is very well conserved between species (FIG. 1).

Figure 2:
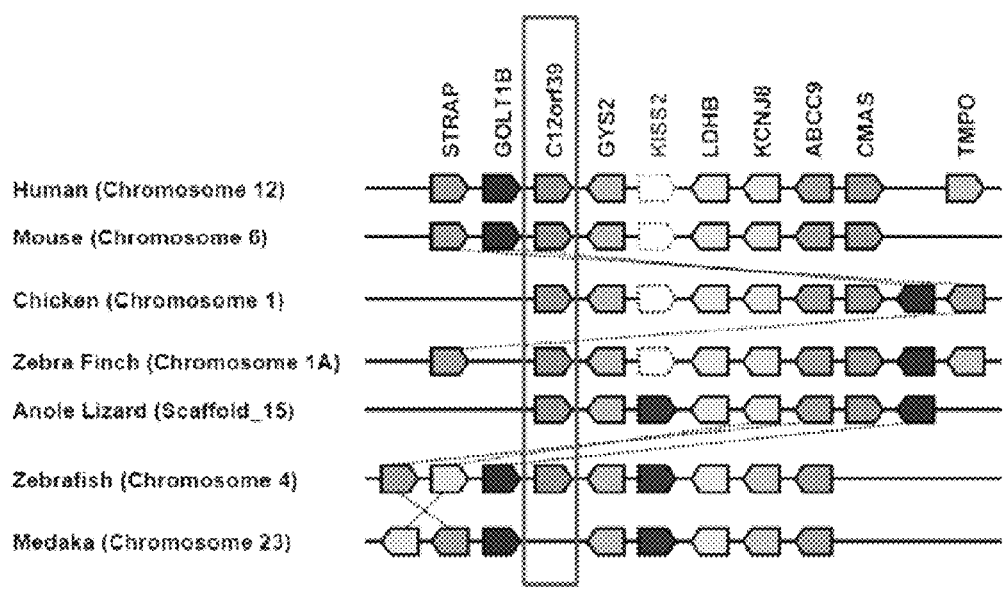
FIG. 2 schematically represents the position of the C12orf39 gene encoding the NQ peptide in genomes of representative vertebrates. Particularly, it shows that the gene group including the C12orf39 gene was very well-conserved.

In addition, since the C12orf39 gene encoding the NQ peptide forms same genome group in representative vertebrates, it is very likely to be responsible for important function in vivo (FIG. 2).

Paralogs of the NQ peptide are found in teleostei and amphibian (FIG. 3). It shows that the present peptide is not only evolutionarily conserved, but also support to the biological clock-related function or a novel function.

Figure 4:
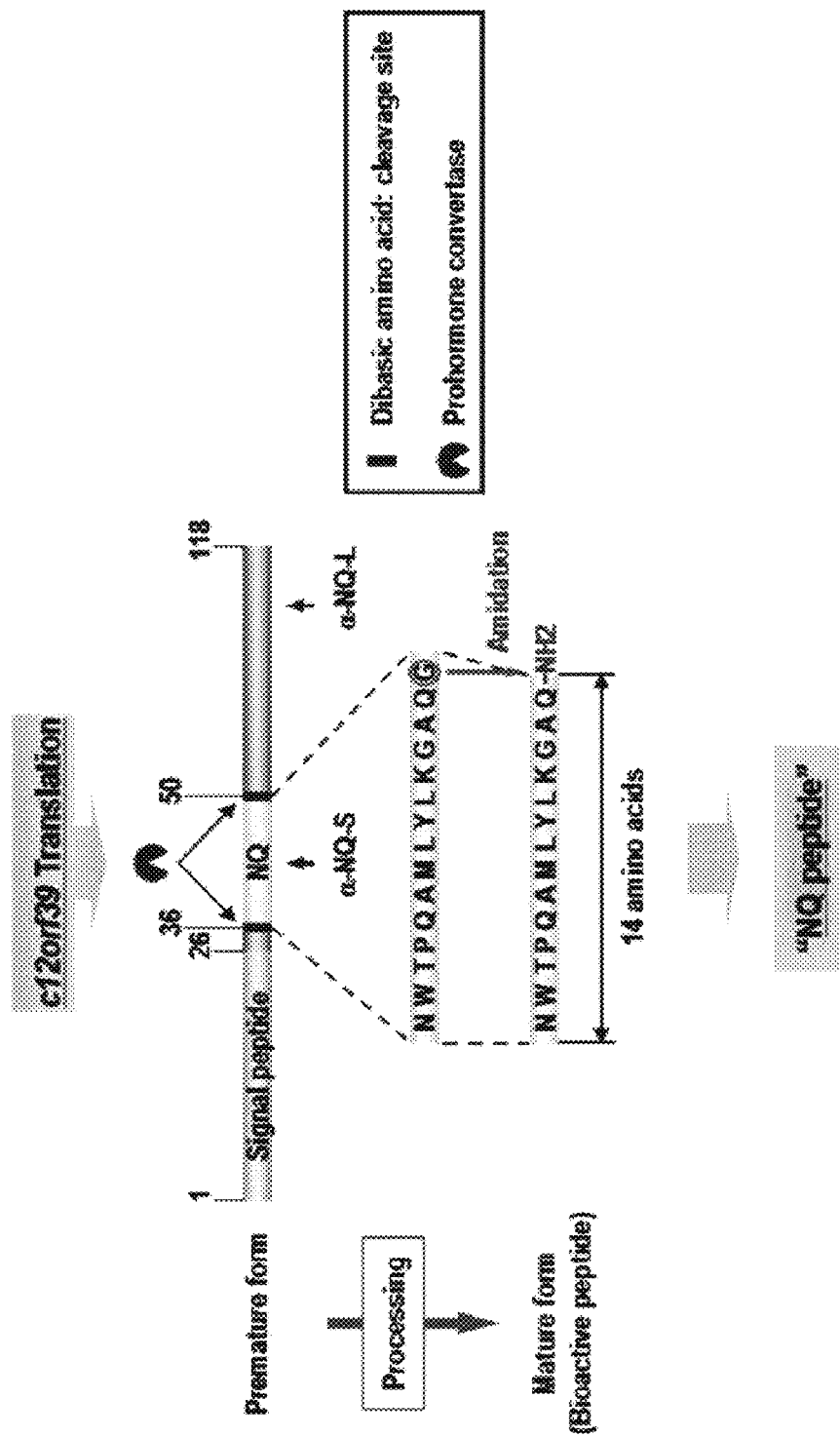
FIG. 4 schematically represents processing of intracellular post-expressional maturation of the NQ peptide. The NQ peptide is expected to undergo the post-transcriptional modification.

The present gene in SEQ ID NO:4 is translated to peptide to form the amino acid structure of FIG. 1. In processing of intracellular post-expressional maturation, it is converted to the mature forms from Asn to Gln or from Asn to His. SEQ ID NO:4 comprising amino acid sequence from Asn to Gln has $NH_2$ at the carboxyl-terminus (FIG. 4).

The present cDNA of the NQ peptide comprising the nucleotide sequence as set forth in SEQ ID NO:9 may be easily prepared by those ordinarily skilled in the art using a primer set having oligonucleotide sequence as set forth in SEQ ID NOs:7 and 8. The detailed method is described in Example 5, but not limited thereto.

Figure 6:
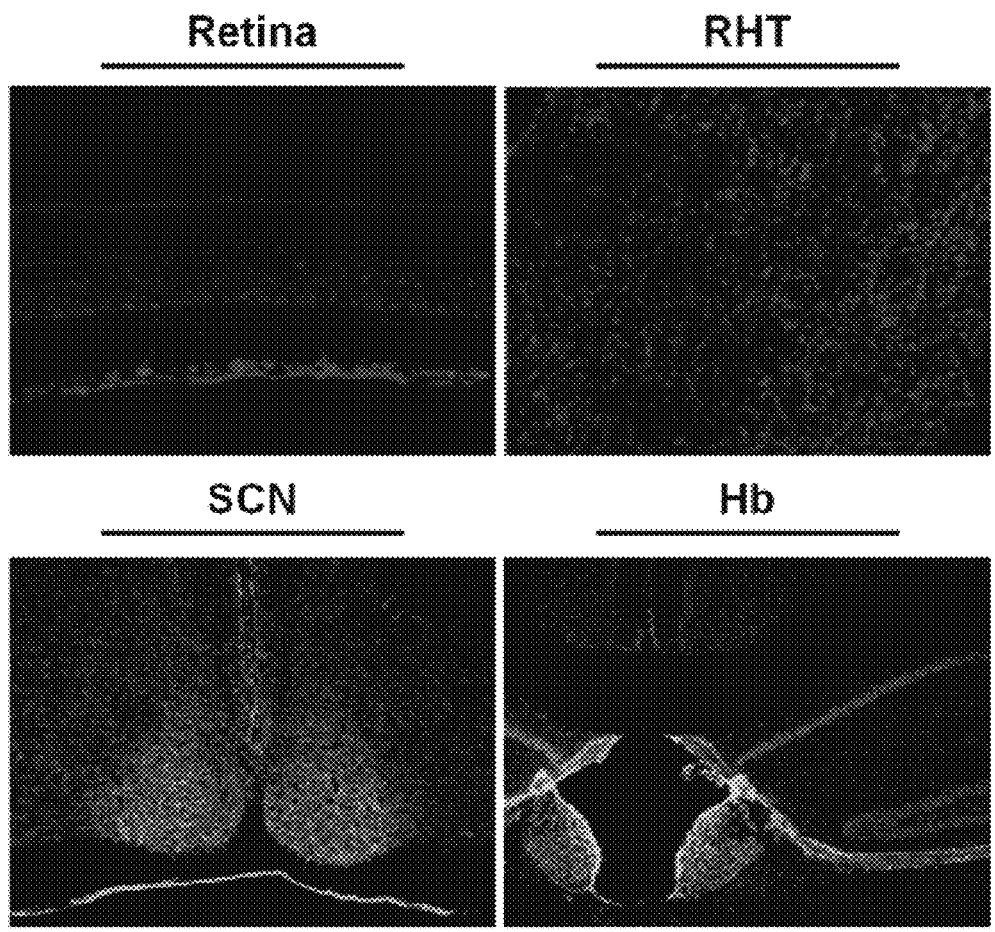
FIG. 6 represents images that the NQ peptide was detected in SCN, habenular nucleus, retina and retino-hypothalamic tract. It shows that the NQ peptide is expressed in certain regions, and may function to relate the biological clock.
Figure 7A:
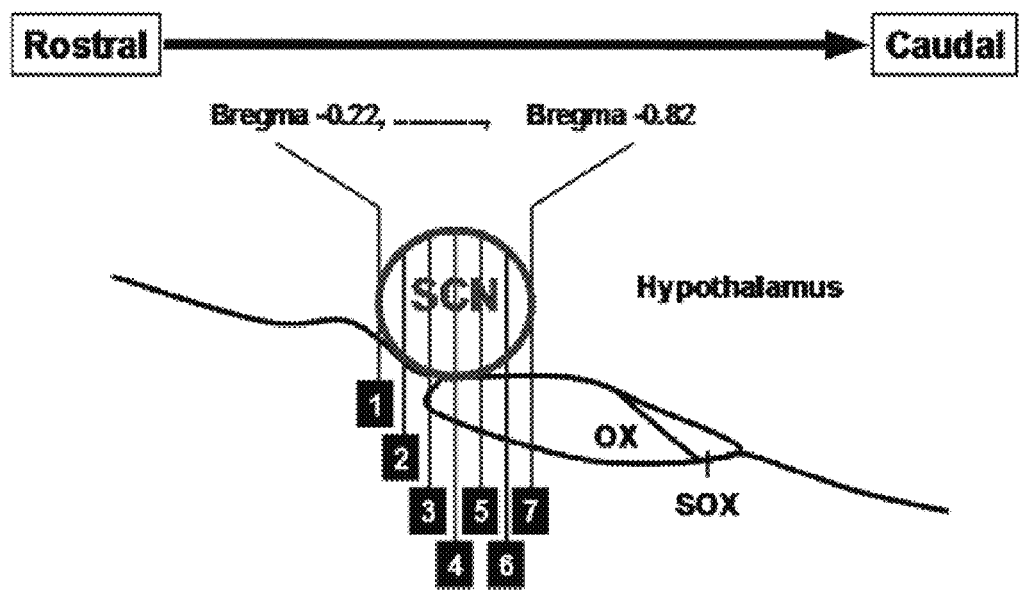
FIG. 7a schematically represents mouse brain coronal section strategy of SCN present in mouse brain.
Figure 7B:
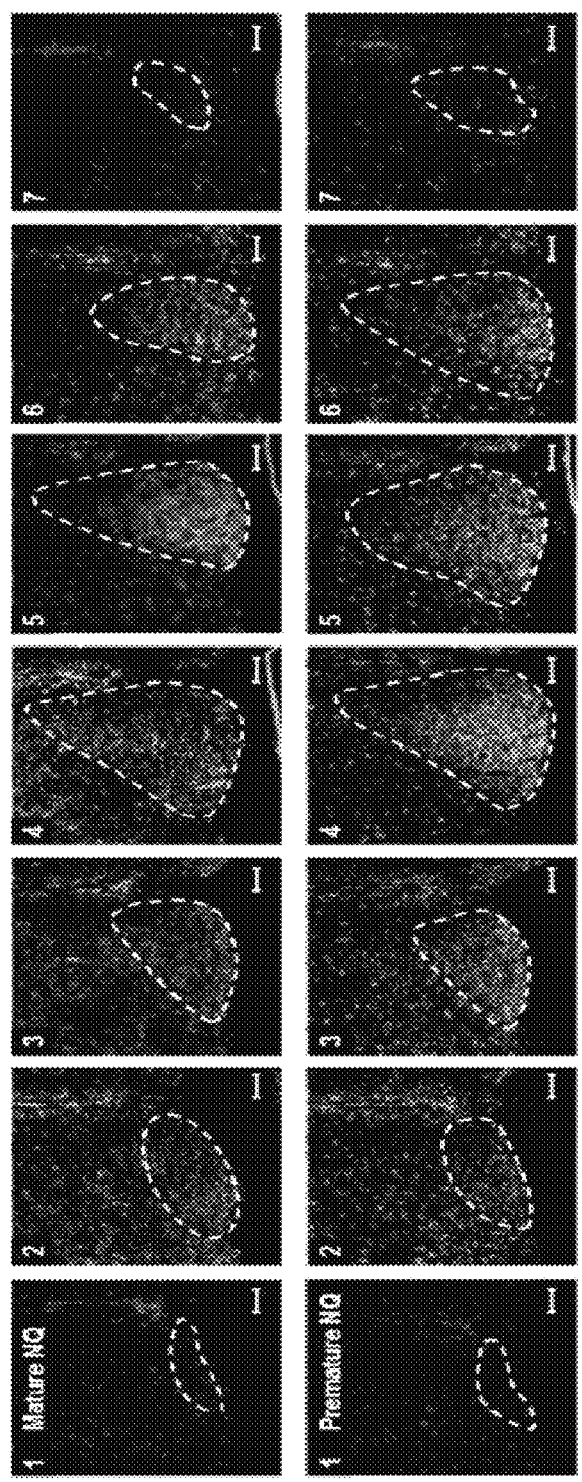
FIG. 7b represents images of analysis for the NQ peptide expression localization in SCN using the mouse brain tissue. It shows that the NQ peptide was strongly detected in ventrolateral region and medial part on rostrocaudal axis.
Figure 8:
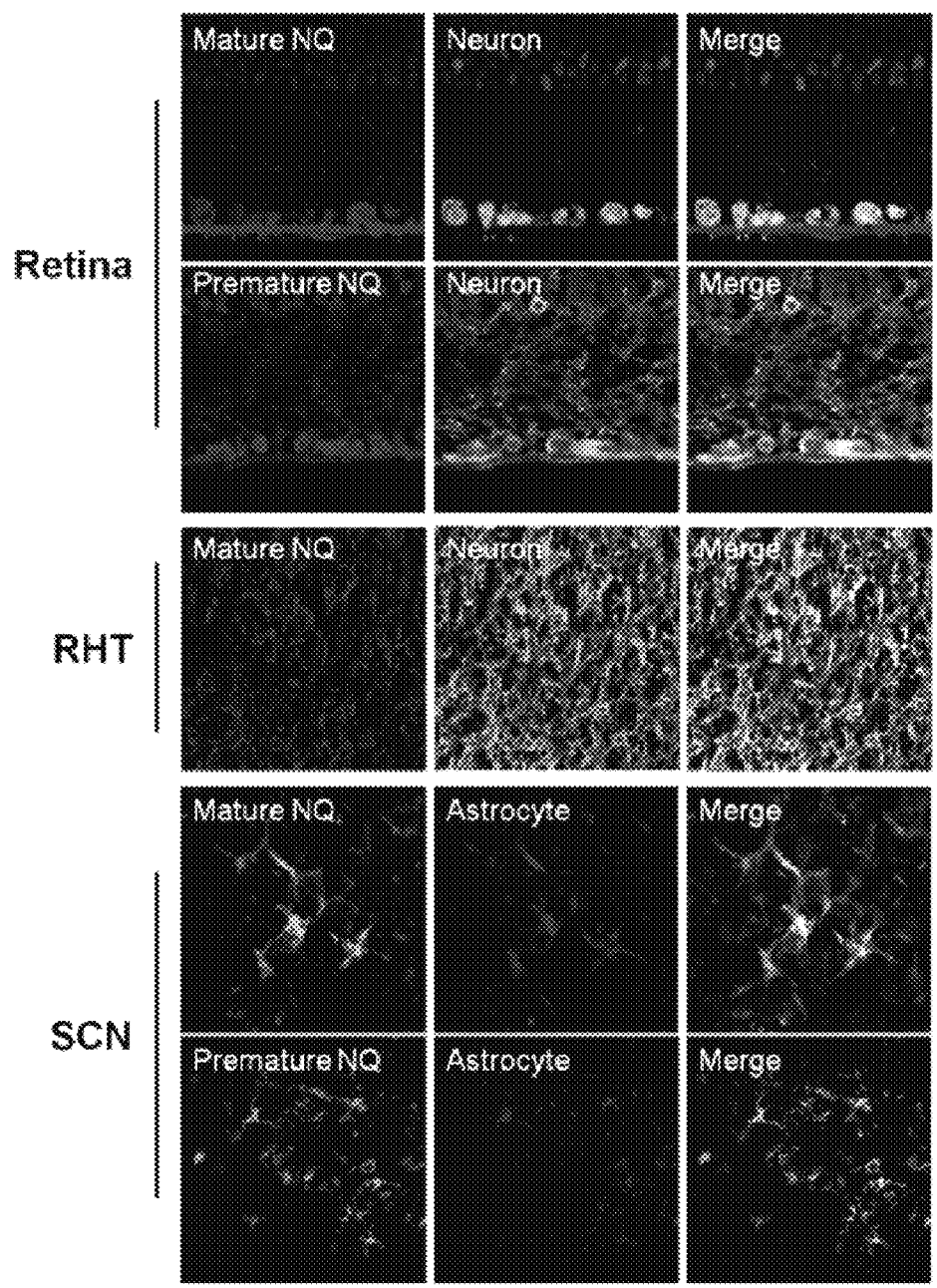
FIG. 8 represents images that the NQ peptide was specifically expressed in astrocytes of SCN and retinal ganglion cells of retina.

According to an embodiment, it is demonstrated that the NQ peptide strongly exists in the core part in which VIPergic neuron abundantly exists or medial part on rostrocaudal axis and ventrolateral region of SCN (FIGS. 6 and 7b). According to another embodiment, it is demonstrated that the NQ peptide is exists in astrocytes of SCN and retinal ganglion cells of retina which is responsible for directly nerve transmission to SCN (FIG. 8).

Figure 9:
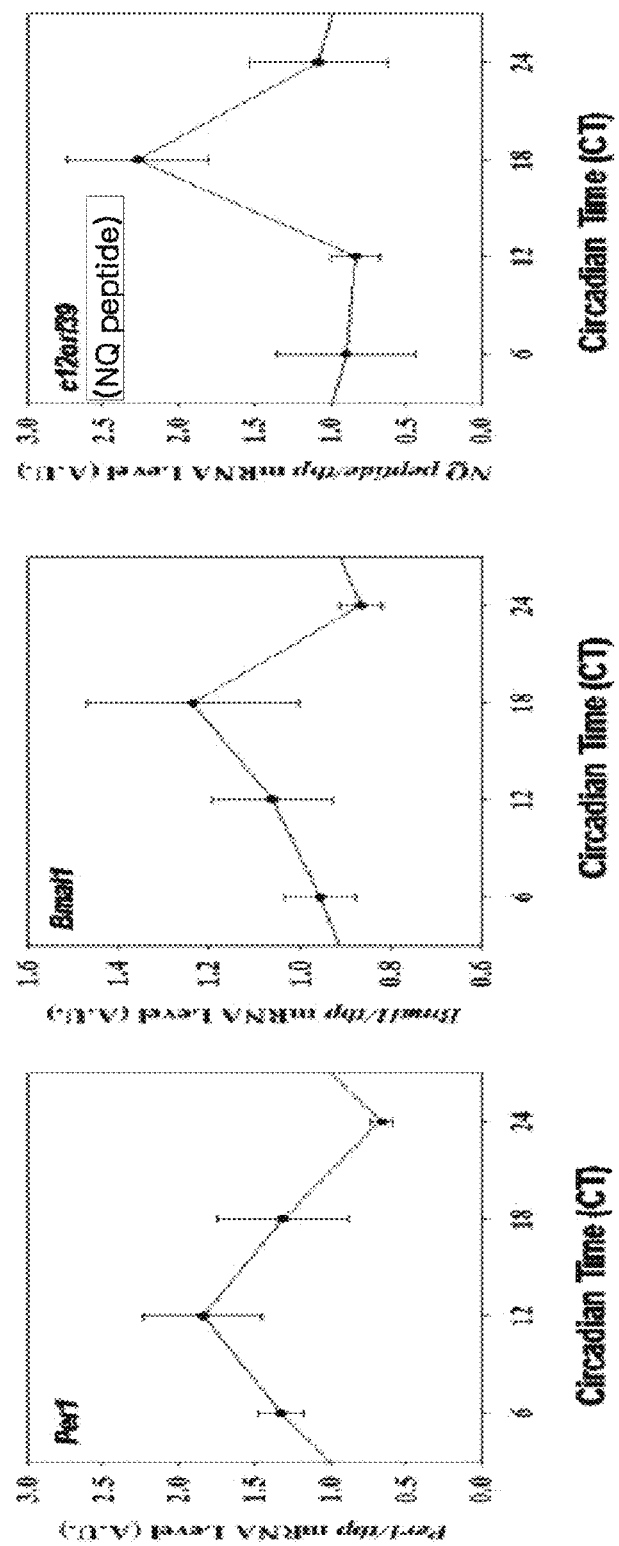
FIG. 9 is graphs showing mRNA expression patterns of bmal1 and per1 as the clock gene or the clock-related gene, and the NQ peptide.

According to another embodiment, it is demonstrated circadian mRNA expression changes of bmal1 and per1 as the clock gene or the clock-related gene, and the NQ peptide (FIG. 9).

Figure 10:
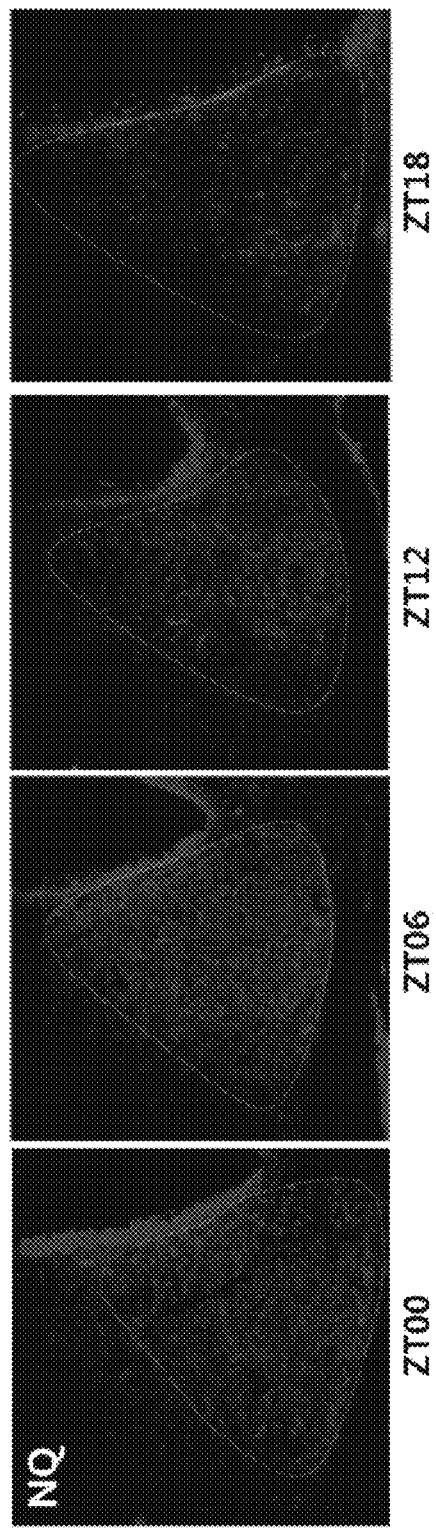
FIG. 10 represents images of time-course mRNA expression level of the NQ peptide in SCN.

As shown in an embodiment, the mRNA expression changes of the NQ peptide as described above induces expression level changes of the protein with the 24-hour intervals wave (FIG. 10). Levels of the NQ peptide secreted from retina which has been known to transmit directly electrical/chemical to SCN were quantitatively analyzed. For this, mice were trained in dark for certain period and treated with different light irradiation times. As a result, the NQ peptide secretion to the light was significantly increased at the circadian time (CT) 23 than that of the CT14 (FIG. 11), indicating that the NQ peptide is light-dependently secreted from retina to SCN.

Figure 12:
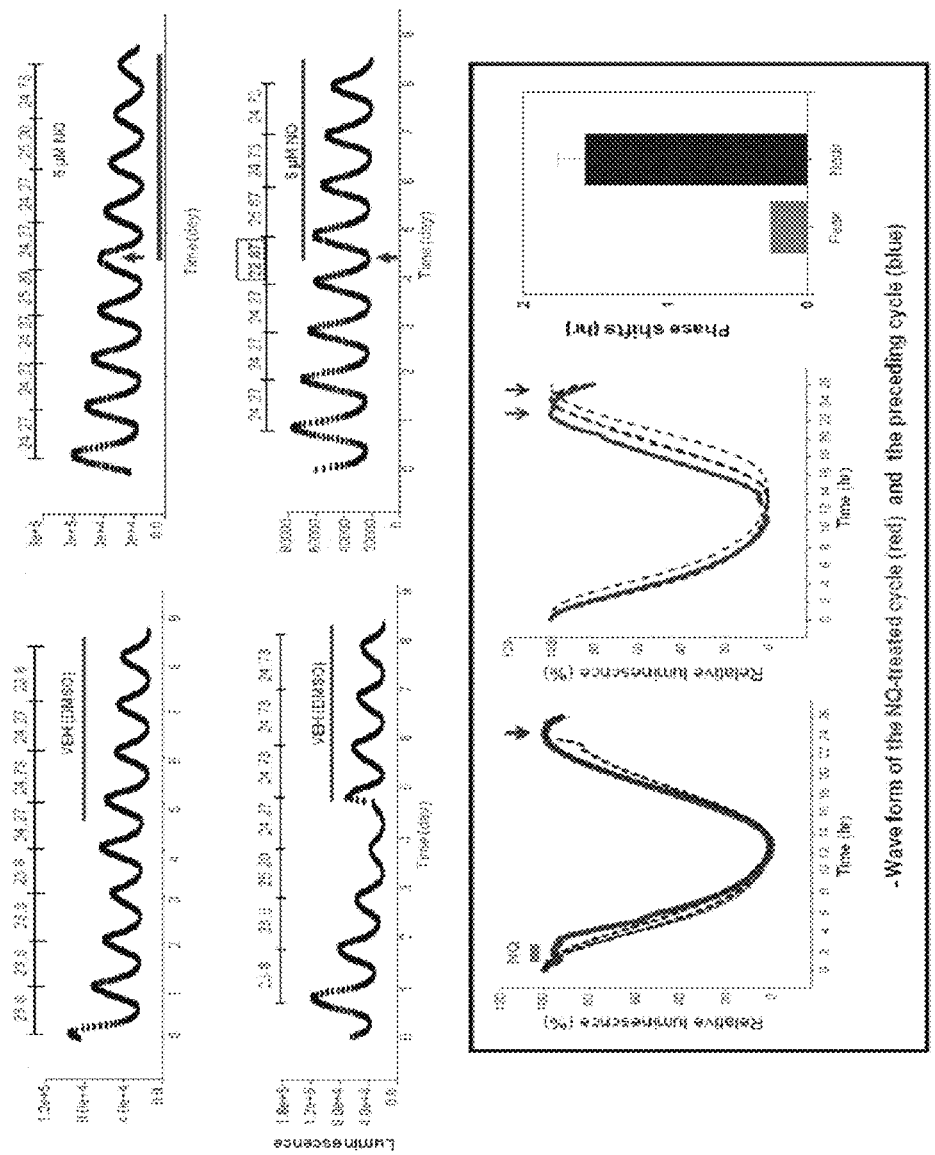
FIG. 12 is graphs that circadian expression of Per2 was changed by the NQ peptide treatment. It shows that the NQ peptide expression directly regulate period of Per2.

In addition, according to another embodiment, the synthetic NQ peptide was treated at the highest point and the lowest point in Per2 phase according to time zone to the mouse brain section. As a result, the phase changes were negligible or barely shown in the treatment at the highest point. In contrast, the free-running period was advanced by approximately 2.80 hours (to approximately 22.87 hours from approximately 24.27 hours) at the lowest point (FIG. 12). Therefore, it could be understood that circadian phase may be regulated by the present peptide or the gene encoding the peptide and cDNA.

Figure 13:
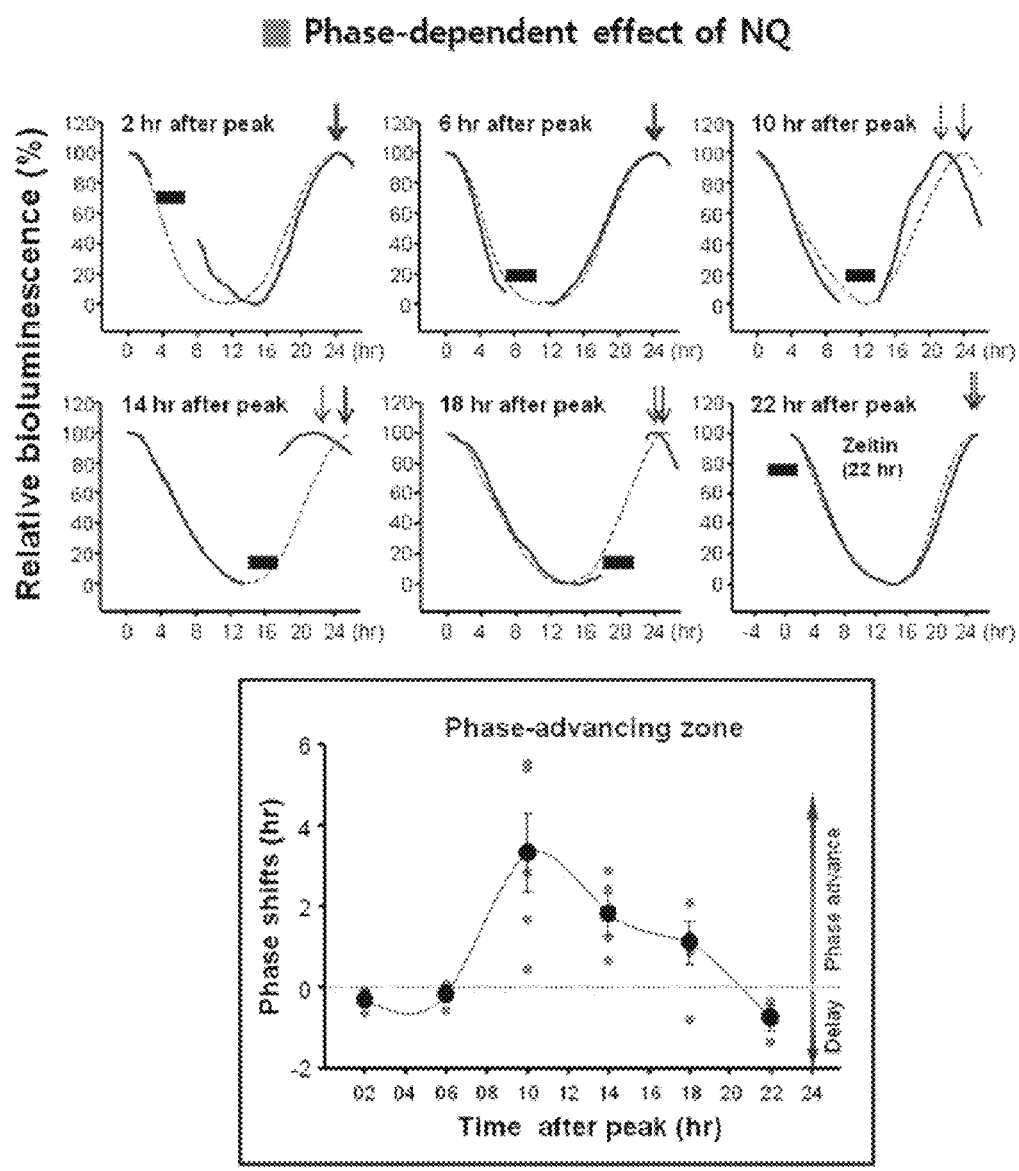
FIG. 13 is graphs showing phase-dependent drug effects of the NQ peptide in Per2. It shows that the highest effect time was at 10 hours after peak.

In order to validate phase-advance effects by the NQ peptide in circadian expression phase, the NQ peptide was treated at each step of Per2 phase (FIG. 13). As a result, where the NQ peptides were treated at 2 and 6 hours after the peak in Per2 activity, effects in the phase advance or the delay were not shown. In contrast, where the NQ peptides were treated at 10, 14 and 20 hours after the peak in Per2 activity, Per2 phase-advancing zone was significantly advanced by the NQ peptide treatment. It shows that the highest effect time was at 10 hours after peak. Meanwhile, where the NQ peptides were treated at 22 hours after the peak in Per2 activity, effects in the phase advance or the delay were negligible. Therefore, it is conclusive evidence that the NQ peptide is functionally related profoundly to the circadian expression of the clock-related protein Per2.

Figure 14:
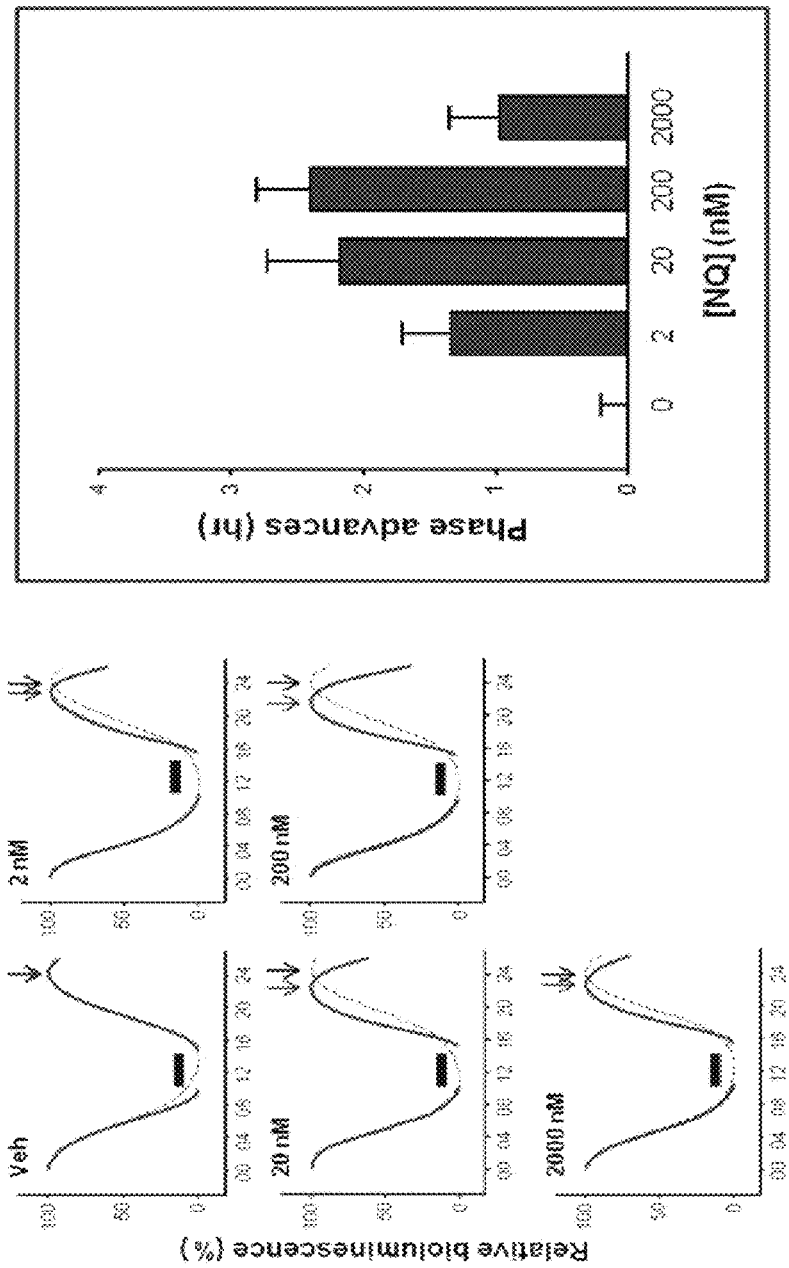
FIG. 14 is graphs showing the NQ peptide dose-dependent circadian changes of Per2. It shows that the highest concentration of the NQ peptide was 200 nM.

According to another embodiment, phase-advance effects of Per2 changed by the NQ peptide dose-dependent manner are validated (FIG. 14). Where the NQ peptide was treated at the lowest point in Per2 phase, it showed phase-advance effects in the NQ peptide dose-dependent manner, and the highest concentration of the NQ peptide was 200 nM.

Figure 15:
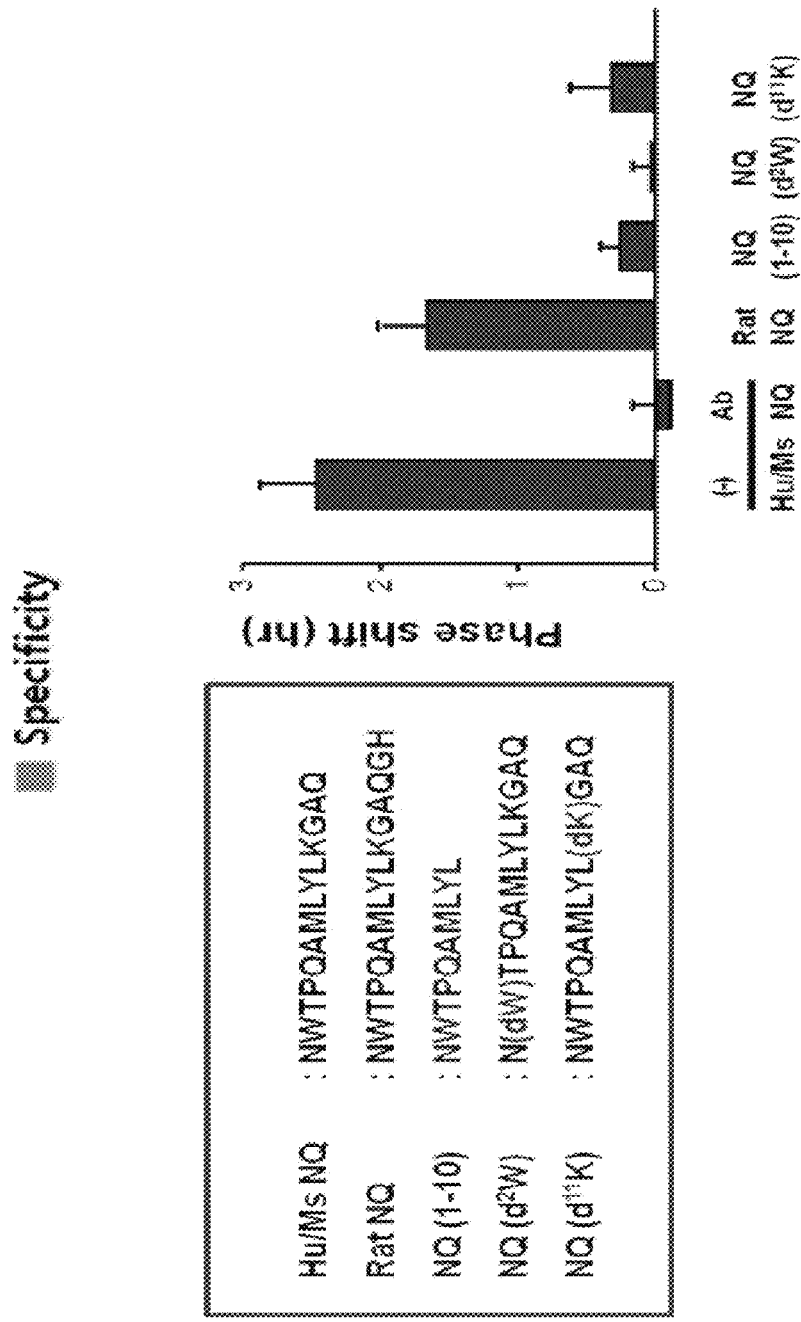
FIG. 15 is graphs showing the physiological activity analysis using the NQ peptide and its mutants. It shows that 2 types of the NQ peptide as set forth in SEQ ID NOs:2 and 3 in mammals changed the Per2 phase. However, where the second Trp residue and the eleventh Lys residue in the amino acid sequence were respectively substituted to optical isomers of D-form or the carboxyl-terminus as set forth in SEQ ID NO:2 was removed, their activities were significantly reduced.

In order to elucidate that certain amino acid of the mature form of the NQ peptide as set forth in SEQ ID NOs:1 and 2 contributes to functional roles of the NQ peptide, the present inventors have synthesized mutants, and those circadian phase change effects were analyzed, respectively (FIG. 15). Whereas the amidated form of the amino acid of the NQ peptide as set forth in SEQ ID NO:2 and the form of the amino acid of the NQ peptide as set forth in SEQ ID NO:3 which is found in rat functionally showed phase-advance effects of Per2, the NQ peptide mutants did not affect circadian changed of Per2 protein. Therefore, it is determined that the two amino acids, i.e., the second Trp residue and the eleventh Lys residue in the sequence of the NQ peptide as set forth in SEQ ID NO:1 play an important role in functional performance of the NQ peptide. In addition, the form of the NQ peptide as set forth in SEQ ID NO:3 found in rats showed that the amidation of the Gly residue following the Gln residue at the carboxyl-terminus of the amino acid sequence as set forth in SEQ ID NO:2 may not be significantly important in functional performance of the NQ peptide.

In the pharmaceutical compositions of this invention, the pharmaceutically acceptable carrier may be conventional one for formulation, including lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methyl cellulose, methylhydroxy benzoate, propylhydroxy benzoate, talc, magnesium stearate, and mineral oils, but not limited to. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in Remington's Pharmaceutical Sciences (19th ed., 1995), which is incorporated herein by reference.

The pharmaceutical composition according to the present invention may be administered orally or parenterally, i.e., by intravenous, subcutaneous, intramuscular, intraperitoneal and transdermal.

A suitable dose of the pharmaceutical composition of the present invention may vary depending on pharmaceutical formulation methods, administration methods, the patient's age, body weight, sex, severity of diseases, diet, administration time, administration route, an excretion rate and sensitivity for a used pharmaceutical composition. Physicians of ordinary skill in the art can determine an effective amount of the pharmaceutical composition for desired treatment. Generally, the pharmaceutical composition of the present invention may be administered with a daily dose of 0.0001-100 mg/kg.

According to the conventional techniques known to those skilled in the art, the pharmaceutical composition may be formulated with pharmaceutically acceptable carrier and/or vehicle as described above, finally providing several forms including a unit dose form and a multi-dose form. The formulation may be in the form of a solution in oily or aqueous medium, a suspension, a syrup, a emulsion, an extract, an elixir, a powder, a granule, a tablet or a capsule, and may further include a dispersant or stabilizer.

The present composition for regulating circadian rhythm may be used for preventing or treating a circadian rhythm disorder.

The circadian rhythm disorder is selected from the group consisting of jet lag syndrome, extrinsic circadian sleep disorder of shift work sleep disorder, delayed sleep phase syndrome (DSPS), advanced sleep phase syndrome (ASPS), non-24-hour sleep-wake syndrome (non-24), intrinsic circadian sleep disorder of Irregular sleep-wake pattern, seasonal affective disorder (SAD), depression, mood disorder of bipolar disorder and insomnia by phase delay or phase advance, but not limited thereto.

The present composition for regulating circadian rhythm may acts in suprachiasmatic nucleus (SCN) or habenula (Hb), further retina, but not limited thereto.

According to Ralph M R et al., SCN is divided into a core part and a shell part. SCN accepts electrical/chemical signals from retina, and interacts with the internal rhythmicity within organism. Therefore, SCN has been known to play an important role in an individual "adaptation for survival" by delicately synchronizing an endogenous biological clock to external environments. Central pacemaker neurons maintain circadian rhythm by rendering to have internal rhythmicity organism itself under condition without external cues [Ralph M R et al., Science, 1990].

In addition, habenular has also been known to relate to circadian rhythm in lower animals and mammals [H. Zhao and B. Rusak, Neurosci., 2005].

Figure 5:
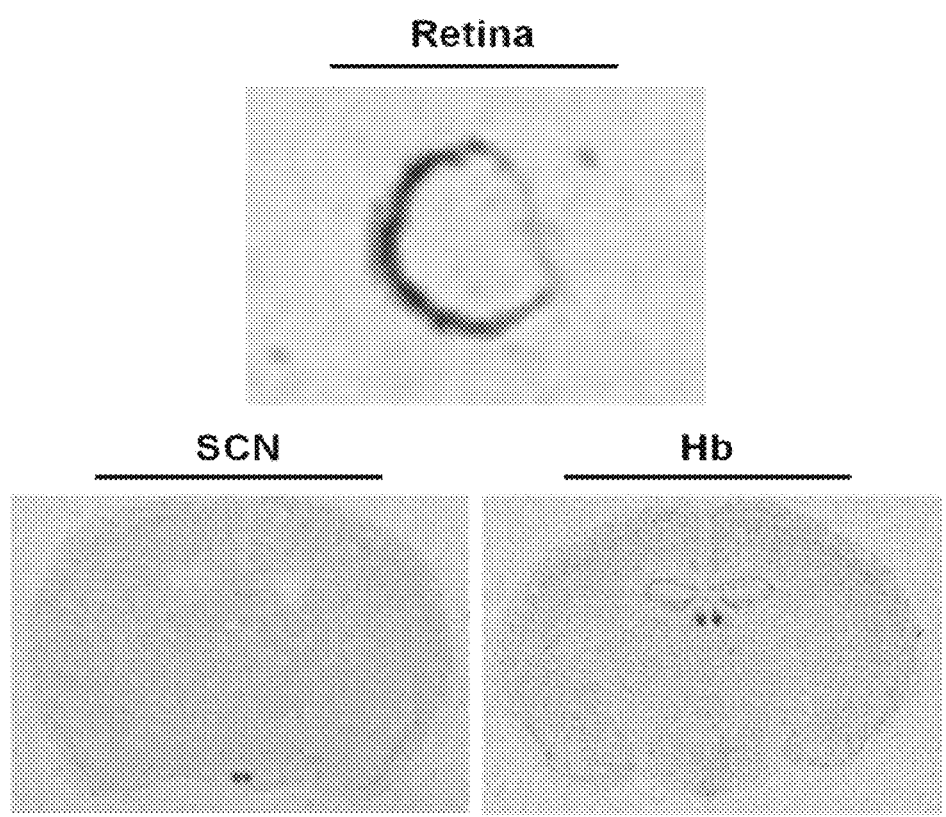
FIG. 5 represents images that mRNA of the C12orf39 gene was detected in SCN, habenular nucleus, and retina. It shows that the NQ peptide is expressed in certain regions, and may function to relate the biological clock.

According to an embodiment, the present mRNA of the C12orf39 gene is strongly expressed in SCN, habenular nucleus, and retina (FIG. 5). It is distinguished that the present invention exists at corresponding location by immunohistochemistry (FIG. 6). It means that the NQ peptide may act in SCN, habenular nucleus, and retina.

The present composition for regulating circadian rhythm may acts in neuroglias or neurons including astrocytes, but not limited thereto.

The present invention provide a composition or a kit for diagnosing a circadian rhythm disorder, comprising: (i) an antibody specifically binding to a peptide comprising the amino acid sequence as set forth in SEQ ID NO:1, a peptide comprising the amino acid sequence as set forth in SEQ ID NO:2, a peptide comprising the amino acid sequence as set forth in SEQ ID NO:2 in which the carboxyl group of the glutamine residue at the carboxyl-terminus is modified by an amino group, or a peptide comprising the amino acid sequence as set forth in SEQ ID NO:3, (ii) an antibody specifically binding to a peptide epitope as set forth in SEQ ID NO:6, (iii) a primer or a probe specifically binding to the C12orf39 gene comprising the nucleotide sequence as set forth in SEQ ID NO:4, or (iv) a primer or a probe specifically binding to cDNA of the NQ peptide comprising the nucleotide sequence as set forth in by SEQ ID NO:9.

The primer or probe may be the oligonucleotide sequence as set forth in SEQ ID NOs:7 and 8.

The present composition or kit for diagnosing a circadian rhythm disorder may further at least one of the other component compositions, solutions or devices suitable for the analysis. Preferably, the kit relates to a kit for detecting a diagnostic marker including essential elements required for performing RT-PCR. An RT-PCR kit may include test tubes or other suitable containers, reaction buffers (varying in pH and magnesium concentrations), deoxynucleotides (dNTPs), enzymes such as Taq-polymerase and reverse transcriptase, DNase, RNase inhibitor, DEPC-water, and sterile water and a suitable carrier. The kits may include a pair of primers specific to gene used as a quantitative control group.

In addition, preferably, the kit may be a DNA chip kit including essential elements required for performing a microarray. The DNA chip kit may include a base plate, onto which cDNAs corresponding to genes or fragments thereof are attached.

In addition, where a mean for measuring the levels of protein is preferably an antibody, the kit may include essential ingredients required for performing ELISA. The ELISA kit may include ingredients capable of detecting bound antibodies, for example, a labeled secondary antibody, chromopores, a suitable carrier, enzyme and its substrate, and an antibody specific to protein of a quantitative control group.

Examples of suitable carriers include, but are not limited to, soluble carriers, such as physiologically acceptable buffers well known in the art, e.g., PBS, insoluble carriers, such as polystyrene, polyethylene, polypropylene, polyester, polyacrylonitrile, fluorine resin, crosslinking dextran, polysaccharide, etc., magnetic microparticles, such as metal-coated latex, paper, glass, metal, agarose, and combinations thereof.

The present invention will now be described in further detail by examples. It would be obvious to those skilled in the art that these examples are intended to be more concretely illustrative and the scope of the present invention as set forth in the appended claims is not limited to or by the examples.

Example 1

Discovery of Peptides for Regulating Circadian Rhythms Using Bioinformatics

Genetic screening of the NQ peptides was achieved through bioinformatic approach model.

Open reading frames (ORF) in approximately 50,000 types of human genome genes were downloaded from Ensemble (http://www.ensembl.org/index.html) and UniprotKB (http://www.uniprot.org/uniprot) by the present inventors. In order to identify molecules with the potential to be bioactive peptides among them, approximately 2,000 types of genes (secretome) with the potential to be secreted from the cells were selected using SignalP3.0 program.

As a result of analysis of the selected ORF based on information in UniprotKB, approximately 600 types of ORF were identified to genes (peptidome) encoding peptides. Although 560 types among them were determined as genes that their functions have been already known, the remaining 40 types were evaluated as genes encoding peptides that their functions have not been yet known.

Among them, the C12orf39 was developed as a gene encoding NQ peptide.

The C12orf39 gene has been found in a variety of vertebrates including humans. Amino acids of the NQ peptide precursors expressed from the C12orf39 gene include the amino acid sequence of the mature NQ peptide including signal peptides. Particularly, it was analyzed that the amino acid sequences cording for the NQ peptides were very well conserved in many species (FIG. 1). For example, amino acid sequences of the NQ peptide in chickens, mice, rats, mammals including humans and zebra fish were apparently well-conserved except that alanine (Ala) is substituted to threonine (Thr) at the carboxyl-terminus in zebra fish and arginine (Arg) is substituted to histidine (His) at the carboxyl-terminus in rats. However, in considering effects of prohormone convertase in intracellular post-transcriptional and post-translational modifications [Rouille Y, Front Neuroendocrinol., 1995], the conversion of amino acids on a dibasic cleavage site into monobasic cleavage site is expected not to affect functional changes of NQ peptides.

The comparative genomic biological assay has been recognized as an experimental model with reliability, of which may validate whether novel genes newly discovered has substantive functions [Robbins, R J, MIT Press, 1996].

Example 2

Genomic Location and Sequence Analysis of NO Peptide

As a result of verifying the location of the C12orf39 from Ensemble and NCBI (http://www.ncbi.nlm.nih.gov/guide/), it was determined that the present gene was evolutionarily conserved in vertebrate species by locating together with gene groups of STRAP (Serine-threonine kinase receptor-associated protein), GOLT1B (Vesicle transport protein GOT1B), GYS2 (Glycogen [starch] synthase, liver), KISS2 (Kisspeptin isoform 2), LDHB (L-lactate dehydrogenase B chain), KCNJ8 (Potassium inwardly-rectifying channel, subfamily J, member 8), ABCC9 (ATP-binding cassette sub-family C member 9), CMAS (N-acylneuraminate cytidylyltransferase), and TMPO (Lamina-associated polypeptide 2, isoforms beta/gamma). Particularly, the present gene C12orf39 gene (SEQ ID NO: 4) was located between GOLT1B and GYS2 genomes. However, the present gene was not observed in medaka which is one species of teleostei. It is predicted that the present gene was lost during long period of an evolutionary process.

Example 3

Paralogs Analysis of NO Peptide

The present inventors have found paralogs of NQ peptide through Ensemble data base. Departing from standpoints from ortholog comparisons (FIG. 1), the present NQ peptides are likely to be a physiologically active peptide and evolutionarily conserved functional peptide because its paralogs exist (FIG. 3).

Where certain gene is undergone evolutionary process for a long period of time, it results in modification of certain DAN sequence, gene duplication or loss. Particularly, by gene duplication, two genes with the same function may exist. However, the other gene than the original functional gene may become subfunctionalized, neo-functionalized or dis-functionalized in a long period time of an evolutionary process. Therefore, the existence of paralogs to the certain gene proves that the gene has been present from very early evolutional time. Accordingly, it may be not expected that the NQ peptide and its paralogs revealed by the present inventors perform only restrictive functions involved in circadian regulation, due to findings of the NQ peptide paralogs.

Example 4

Maturation of NO Peptide

The NQ peptide was estimated to consist of the total 14 amino acids (SEQ ID NO: 2) predicted as a functional form in vivo, which is generated by transcription of a propeptide having the total 118 amino acids and then intracellular post-translational modification to cleave dibasic cleavage sites of the propeptide by prohormone convertase (FIG. 4).

Therefore, the amino acid sequence of the mature NQ peptide expressed from the C12orf39 gene (SEQ ID NO: 4) was predicted to be in the form of "NWTPQAMLYLK-GAQ-NH2". As it has asparagine (Asn) at the N-terminus and glutamine (Gln) at the carboxyl-terminus, the present inventors called the bioactive peptide "NQ peptide".

In addition, the propeptide structure of the NQ peptide has a gene sequence encoding a signal peptide at the amino-terminus as a signal for extracellular secretion. In maturation, the NQ peptide undergoing maturation is subjected to removal of a glycine residue at the carboxyl-terminus to provide an amide group ($-NH_2$), which make it expectable to have functions as a physiologically active peptide. On the other hand, for rats, the his residue in SEQ ID NO:3 was positioned at the carboxyl-terminus instead of the amide group by maturation process of NQ peptides.

Example 5

C12orf39 Gene Expression Profiling by In Situ Hybridization 6-week-old male C57BL/6 mice were purchased from dhbiolink (http://www.dhbiolink.com). The mice were properly fed a food (chow) and water. The environments for animals were maintained at 20-24° C. and relative humidity 40-70% on cages. Wild type mice were trained under 12 hours light/dark cycle with the light initiation 8:00 am and the light termination 8:00 pm.

All experiments are designed to use the small number of experimental animals, performed with anesthesia method in accordance with institutional guidelines to minimize pain, approved by the Animal Care and Use Committee of the Korea University (KUIACUC-08).

8-week-old male mice maintained by the method described above were intraperitoneally anesthetized with urethane 0.5 cc/100 g and sacrificed to obtain brain and eyes. The organs were surgically excised, and the tissues were rapidly frozen with isopropanol solution on dry ice. The frozen organs were sectioned in a thickness of 12 µm and thaw-mounted on glass slide coated with TESPA (sigma-Aldrich, St. Louis, Mo., USA), and fixed in PBS (Phosphate buffered saline) containing 4% PFA (paraformaldehyde). The slide were acetylated with 0.1 M triethanolamine/0.9% NaCl (pH 8.0) containing 0.25% acetic anhydride, dehydrated and defatted using ethanol and chloroform, followed by drying in air.

The sectioned tissues were hybridized using $^{35}$S-labeled probes at 55° C., and washed with 2×SSC solution at room temperature.

After RNase treatment, the slides were serially washed with 2×SSC, 1×SSC, 0.5×SSC, 0.1×SSC solutions containing 1 mM dithiothreitol at room temperature for 10 min, respectively. Finally, the slide were dehydrated, air-dried and exposed to X-ray film (Biomax MR, Kodak, Rochester, N.Y., USA).

On the other hand, in order to generate probes, total RNA extracted from cerebral cortex of adult mice reverse-transcribed using reverse transcriptase and random hexamer as primer to synthesize cDNA (complementary DNA, SEQ ID NO: 9), and cloned into T-vector (Promega, Madison, Wis., USA). The primers used in PCR are shown in Table 1. In vitro transcription system (Promega, Madison, Wis., USA) was performed using the cloned T-vector as template under containing of α-[$^{35}$S] UTP (Amersham Pharmacia Biotech, Piscataway, N.J., USA). The anti-sense riboprobes of the generated label were purified to use this hybridization.

TABLE 1

| Target gene | Primer sequences | Product size (bps) | Positions | Accession number |
|---|---|---|---|---|
| C12orf39 | up: CGA CTC TCT GAG AAG AGG AAC (SEQ ID NO: 7)<br>down: TCT CAG CCT TGA CAC GT (SEQ ID NO: 8) | 499 | 88-586 | XM_620381 |

As a result of the hybridization, mRNA of the NQ peptides was strongly expressed specifically in SCN, habenular, and retina (FIG. 5).

Habenular has also been known to relate to circadian rhythm in lower animals and mammals [H. Zhao and B. Rusak, Neurosci., 2005]. Because vasopressinergic efferent nerve from SCN is not only connected to pineal gland secreting melatonin which is related to circadian rhythm, but also shown the nerve innervation which is directly connected in habenular nucleus, particularly, lateral habenular nucleus (LHb) [Buijs, Cell Tissue Res., 1978; Ronnekleiv and Moller, Exp. Brain. Res., 1979]. Since nerves transmitting direct signals to hypothalamus SCN are distributed in retina, the extrastimulation of light may be quickly transmitted through retino-hypothalamic tract [Jens Hannibal, Cell Tissue Res., 2002].

In addition, since receptors of melatonin are present in LHb, all of SCN, habenular nucleus and pineal gland are expected to an axis related to circadian rhythm [Sato T et al., Cell Tissue Res., 1991; Weaver D R et al., J. Neurosci., 1989; Zamorskii II and Pishak V P, Bull. Exp. Biol. Med., 2000].

Meanwhile, these results assume new expression pattern to presence region of NQ peptide which is observed in the central nervous system, and substantially different from recent results that NQ peptide have been mainly observed in the peripheral tissues [Olivier Mirabeau, Genome. Res., 2007; Bingbing Wan, Biosci. Rep., 2010; Marcin Rucinski, Peptides, 2010]. Ultimately, it is first suggested that NQ peptides are likely to be substances related to circadian rhythm [Olivier Mirabeau, Genome. Res., 2007; Bingbing Wan, Biosci. Rep., 2010; Marcin Rucinski, Peptides, 2010].

Example 6

NQ Peptide Expression Analysis by Immunohistochemistrty 8-week-old male mice maintained by the method described above were intraperitoneally anesthetized with urethane 0.5 cc/100 g. To obtain brain, the chest skin was incised, and left cardiac ventricle was connected to Ringer needle. Then, 200 mL of 0.9% saline solution was supplied to remove blood, and 200 mL of 0.9% saline solution containing 4% paraformaldehyde was perfused to fix. To obtain retina and retino-hypothalamic tract, the eyes were excised, and pupil was holed with 26 G needle. Then, 0.9% saline solution containing 4% paraformaldehyde was supplied to fix for 2 hours.

The fixed brain was isolated, post-fixed in 0.9% saline solution containing 4% paraformaldehyde for 24-48 hours, and treated in 0.9% saline solution containing 30% sucrose for 24 hours. The fixed retina and retino-hypothalamic tract tissues were treated in 0.9% saline solution containing 30% sucrose for 3 hours. The retina tissue was incised crosswise from the holed pupil to remove lens. Solution mixed with 30% sucrose and OCT compound at a ratio of 3:2 was supplied as much as volume of the removed lens to prevent collapse of tissue. Then, the brain and retina were rapidly frozen on dry ice using mold containing OCT compound, and stored at −80° C. until use.

In order to elucidate NQ peptide-specific expression localization and intensity in the brain and retina by immunohistochemistry, rabbit-polyclonal antibody α-NQ-S and rabbit-polyclonal antibody α-NQ-L which are reactable to NQ peptide were prepared by the conventional methods known in the art.

The stored tissues were sectioned in a thickness of 30 μm by cryostat microtome, thaw-mounted on glass slide, and dried at room temperature for one day. Each slide was washed with PBS for 30 min, and blocked for 1 hour in PBST solution (PBS containing 0.1% TritonX-100) containing 10% goat-serum. In order to reduce nonspecific antigen-antibody reaction and distinguish NQ-specific expression localization with more accuracy, NQ antibodies and the solution were adjusted to a ratio of 1:500.

Each antibody was incubated with the tissue at room temperature for overnight. After the primary antibody-antigen reaction, the brain tissue was washed 3 times with PBS for 10 min. FITC-conjugated goat-anti rabbit secondary antibody (Molecular Probes, Eugene, Oreg.) and Cy3.5-conjugated goat-anti mouse secondary antibody (abcam) were used as secondary antibodies to NQ peptide by diluting at a ratio of 1:1,000 and 1:500, respectively. At the same time, Hoechest33342 (Molecular Probes, Eugene, Oreg.) was used to stain nucleus at a ratio of 1:20,000.

After the secondary antibody-antigen reaction, the brain tissue was washed 3 times with PBS for 10 min, dried in dark for 30 min, mounted with crystal/mount solution (Biomeda, USA), and covered by cover glass to prepare a specimen. Zeiss LSM 510 confocal microscopy was used for fluorescence observation of the specimen.

Interestingly, it was determined that NQ peptide (including the amino acid sequence as set forth in SEQ ID NO:2 in which the carboxyl group of the glutamine residue at the carboxyl-terminus is modified by an amino group) in protein level was also expressed in SCN, habenular nucleus, retina and retino-hypothalamic tract, like the results of hybridization histochemistry (FIG. 6).

In certain genes, protein expression localization is different from mRNA expression localization due to post-transcriptional or post-translational modification [Cheryl L. Wellington et al., Lab. Invest., 2002]. However, in the present invention, expression localizations of mRNA and protein were shown as the same portion and pattern, whereby it was determined that the present substance is stably expressed in vivo.

The results of Examples 5 and 6 suggest presences, localizations and intensities of NQ peptide expression in brain and eye tissues, and they support the present hypothesis that the present substance is related to circadian rhythm in vivo.

Example 7

NQ Peptide Expression Localization Analysis in SCN by Mouse Brain Coronal Section Strategy and Immunohistochemistrty SCN is responsible for controlling circadian rhythm. SCN is situated in the anterior part of the hypothalamus immediately dorsal, or superior to the optic chiasm bilateral to the third ventricle. In mouse, SCN is a tiny region situated at 600 µm on rostrocaudal axis, 300 µm on left-right axis and 350 µm on dorsoventral axis [Eric E. Abrahamson and Robert Y. Moore, Brain Res., 2001; Expedito S. Nascimento Jr., Brain Res., 2010].

This analysis for NQ peptide expression localization in SCN is very important to predict the correlation between NQ peptide and certain neurons.

Because SCN has VIPergic neuron which is abundantly present in the core part corresponding to ventromedial region, and AVPergic neuron which is abundantly present in the shell part corresponding to dorsolaterl region, the correlation with circadian rhythm may be analyzed [Yuriko Ban, J. Neurosci., 1997; Martin smith, J. Chem. Neuroanat., 1996].

In addition, it has been known that these neuropeptides show different expression patterns in anterior part and posterior part of SCN [Yuriko Ban, J. Neurosci., 1997]. According to literatures of Stevens and Holtmaat, the structures of neurons which are expressed these neuropeptides were changed in accordance with circadian changes in real time [Beth Stevens, Neuro signal, 2008; Anthony J G D Holtmaat et al., Neuron, 2005].

Therefore, there is the potential for that the correlation and change factor between neuron-neuron or neuron-glia is due to the NQ peptide under such the circadian circumstances, the analysis for NQ peptide expression localization in SCN is very important.

For this reason, the present inventors have established to protocol that the mouse brain prepared by the method as described above are sectioned in a thickness of 40 µm from anterior part to posterior part of SCN (FIG. 7a), and they have found to NQ peptide expression patterns using fluorescent-labeled secondary antibodies (FIG. 7b).

As the present substance exists in two different structures of premature form or mature form, different antibodies which may recognize different epitopes and react immune responses were used as listed in Table 2.

TABLE 2

| Antibody name | Epitope | Form |
|---|---|---|
| α-NQ-S | NWTPQAMLYLYGAQ-NH2 (SEQ ID NO: 5) | Mature, Premature |
| α-NQ-L | SLEKSQKGADEGGNFDKSELLEDR (SEQ ID NO: 6) | Premature |

Generally, NQ peptides of premature form and mature form were strongly expressed. Particularly, they were strongly expressed in 4 and 5 portions (medial part) on rostrocaudal axis, which were the core part of SCN. In addition, they were relatively high-expressed in ventral region on dorsoventral axis and lateral region on left-right axis.

Since these results showed that NQ peptides were particularly strong-expressed in VIPergic neurons and AVPergic neurons which are positioned in the core part of SCN, there is the potential for that the present substance plays a pivotal role related to circadian function in the correlation between neuron-neuron or neuron-glia.

Example 8

NQ Peptide Expression Pattern and NQ Peptide-Expressing Cell Identification in SCN, Retina and Retino-Hypothalamic Tract of Mouse In the present Example, the present inventors elucidated that what kind of cells express the NQ peptides expressed in the core part of SCN and retina. In order to identify cells synthesizing the NQ peptides, immunohistochemistry was performed by double-treating primary antibodies to the NQ peptides to the prepared mouse brain tissue slides together with mouse GFAP (Cell Signaling Technology, UK) as primary antibody to GFAP (Glial fibrillary acidic protein) which is a marker for astrocytes in SCN, and mouse TuJ1 (Covance) or mouse NeuN (Milipore) as primary antibody to Neuron-specific class III beta-tubulin, TuJ1 or Neuronal nuclei, NeuN which are a marker for retinal ganglion cells in retina, respectively.

Prior to the antibody treatments, each slide was blocked for 1 hour in PBS solution containing 10% goat-serum. The antibodies including antibodies to the NQ peptide were adjusted to a ratio of 1:500. Each antibody was incubated with the tissue at room temperature for overnight.

After the primary antibody-antigen reaction, the brain, retina and retino-hypothalamic tract tissues were washed 3 times with PBS for 10 min at room temperature. FITC- or Cy3.5-conjugated goat-anti rabbit secondary antibodies were used as secondary antibodies to primary antibodies of the NQ peptide by diluting at a ratio of 1:1,000, respectively. FITC- or Cy3.5-conjugated goat-anti mouse secondary antibodies were used as secondary antibodies to primary antibodies of the remaining antibodies by diluting at a ratio of 1:500, respectively. At the same time, Hoechest33342 (Molecular Probes, Eugene, Oreg.) was used to stain nucleus at a ratio of 1:20,000. After the secondary antibody-antigen reaction, the tissues were washed 3 times with PBS for 10 min, completely dried at room temperature, mounted with crystal/mount solution, and covered by cover glass to prepare a specimen. Confocal microscopy was used for fluorescence observation of the specimen.

As a result, the NQ peptides (comprising the amino acid sequence as set forth in SEQ ID NO:2 in which the carboxyl group of the glutamine residue at the carboxyl-terminus is modified by an amino group) identified in SCN were corresponded exactly to astrocytes. Meanwhile, the NQ peptide synthesis and expression were limitatively elucidated in only several astrocytes, not all astrocytes. It means that the NQ peptides are differentially expressed quantitatively in astrocytes according to circadian changes. In addition, unlike SCN, the NQ peptides were expressed in several retinal ganglion cells and retino-hypothalamic tract (FIG. 8).

These results were further supported that the NQ peptide is related to circadian regulation, by literatures as follows.

For example, transcription factor c-Fos was expressed by the light stimulus in astrocytes as well as neurons. Besides, it has been reported that expressions of astrocytes marker protein GFAP also were quantitatively regulated by circadian rhythms (Bennett et al., NeuroRep., 1994). In addition, excitatory signals of Glu generated by the light stimulus in eye are transmitted into SCN through retino-hypothalamic tract. It has been demonstrated that there is an interrelationship between genesis of retino-hypothalamic tract and quantitative-increases of astrocytes in terms of embryological development (Lavialle and Serviere, Dev Brain Res., 1995). It has been proven that the per gene expression of astrocyte well-known in vertebrates was observed in *drosophila*, and its expression showed circadian rhythms (Ewer et al., J. Neurosci., 1992).

In addition, it has been found that both of neurons and astrocytes were excited by glutamate to increase the amount of calcium in endoplasmic reticulum (van den Pol and Dudek, Neurosci., 1993). Besides, systematic change in astrocytes showing circadian rhythms was determined to be marker for the biological clock activity (Lavialle and Servier, Neurorep., 1993). It has been proven that the biological clock in neurons was collapsed where cellular metabolism in glia cells was suppressed (Prosser et al., Brain Res., 1994).

On the other hand, astrocytes as cell membrane receptor have adenosine receptor type A1 (A1 receptor) which is a kind of G protein-coupled receptor (GPCR). Although the binding between the receptor and its ligand adenosine induced the sleep with the mechanism of increasing gliotransmission in cell levels of animal models, mutual functional deficiency result in loss of the sleep function to cause memory and cognitive defects (Halassa et al., Neuron, 2009).

The NQ peptides derived from the retinal ganglion cells as well as astrocytes show the possibility that the NQ peptides as chemical signals such as glutamate may be transmitted to SCN when the cells detected the light stimulus from outside. For this reason, rapid expressions of transcription factors such as c-fos induced by the light may be promoted.

The retinal ganglion cells and SCN were interconnected each other and the NQ peptides were expressed in the retinal ganglion cells as a kind of neuron, whereby the NQ peptides are likely to be a mediator directly transmitting external cues and the light information to SCN through retina-retinohypothalamic tract. Therefore, it is expected that the NQ peptides may contribute to individual adaptation and survival by delicately synchronizing an endogenous biological clock to external environments.

Taken together the above literature, it could be determined that astrocytes present in central nervous system not only are in charge of functions for supporting neurons, but also independently directly connected to circadian function significantly. Therefore, it is expected that the network of astrocytes of brain and retinal ganglion cells of retina shows synergic effects for performing circadian function of the NQ peptides.

Example 9

Time-Course mRNA Expression Pattern of the Biological Clock-Related Marker Genes Per1 and Bmal1, and C12orf39 Encoding the NQ Peptide In order to elucidate how the NQ peptides expressed from astrocytes are changed according to circadian effects, a sample after reverse transcription reaction prepared by the method as described above was diluted to 5 times using 1 mM Tris, and pooled to use as a standard of real-time PCR. Then, it was diluted secondly to 15 times, and used as template real-time PCR to quantification.

LightCycler Version 1.5 (Roche, Salt Lake City, USA) was used for Real-time PCR. 2×SYBR Premix EX Taq (Takara, RR041A) was used to amplify. 2 µL of each of the secondly diluted sample or the standard was added in 8 µL of PCR Master Mix containing 2.2 µL of sterile distilled water, 0.4 µL of sense primer, 0.4 µL of PCR Reverse Primer and 5 µL of 2×SYBR to use. Each gene expression level was quantified by calibrating with mRNA level of the tata binding protein (tbp), nucleotide sequences of primers used in measurement are shown in Table 3.

TABLE 3

| Target gene | Primer sequence | Product size (bps) | Position | Accession number |
|---|---|---|---|---|
| C12orf39 | Up: AGA GCC GTA GGA AGG AGC TT (SEQ ID NO: 11)<br>Down: TTT TCC AAG GAA GCC AGA AA (SEQ ID NO: 12) | 112 | 170-281 | XM_620381 |
| Per1 | Up: GTG TCG TGA TTA AAT TAG TCA G (SEQ ID NO: 13)<br>Down: ACC ACT CAT GTC TGG GCC (SEQ ID NO: 14) | 142 | 39-180 | NM_001159367 |
| Bmal1 | Up: GGC CAT CAG TAA AGG TGG AA (SEQ ID NO: 15)<br>Down: GGT GGC CAG CTT TTC AAA TA (SEQ ID NO: 16) | 115 | 1284-1398 | NM_007489 |
| TBP | Up: GGG AGA ATC ATG GAC CAG AA (SEQ ID NO: 17)<br>Down: CCG TAA GGC ATC ATT GGA CT (SEQ ID NO: 18) | 113 | 239-351 | NM_013684 |

As a result, NQ mRNA expression level showed a peak at CT18 (FIG. 9). There were differences in the Per1 and Small expression patterns which have been previously known. The mRNA expression level peak time of the NQ peptides highly expressed in the core part of SCN (FIG. 6) was similar to that of vasoactive intestinal polypeptide (VIP) which is expressed in anatomical similar region to that of the NQ peptides [Hugues Dardent et al., Molecular brain res., 2004].

Example 10

Circadian Expression Patterns of the NQ Peptide

Changes of the NQ peptide expression levels in astrocytes of SCN were circadianly observed by immunohistochemistry. Mice were trained for 2 weeks under 12:12 LD condition in which the light initiation was 09:00 (ZT00) and the light termination was 21:00 (ZT12). The mice brains were prepared by the method as described above. The NQ peptide expression levels were measured at time points with six hours intervals ZT00, ZT06, ZT12 and ZT18. The mice trained according to the method were intraperitoneally anesthetized. ZT12 and ZT18 were trained in dark. The anesthetized mice were perfused and their brain tissues were isolated. The tissues were fixed in paraformaldehyde for one day, and rapidly frozen with OCT compound on dry ice. The frozen tissues were sectioned in a thickness of 40 mm to prepare samples.

The samples were washed with PBS for 30 min, and blocked for 1 hour in PBST solution containing 10% goat-serum. Primary antibody to the mature or premature forms of the NQ peptides was incubated with the tissue at room temperature for 3 hours. In order to reduce nonspecific antigen-antibody reaction, the tissue was washed 3 times with PBS. The tissues were treated with Cy3.5-conjugated goat-anti rabbit secondary antibody diluted at a ratio of 1:500 at room temperature for 1 hour, and washed 3 times with PBS. The tissues were thaw-mounted on glass slide, dried in dark for 30 min, mounted with crystal/mount solution, and covered by cover glass to prepare a specimen. The specimen was observed with fluorescence microscopy.

All of the mature and premature forms of the NQ peptides were strongly expressed in SCN. The expression levels of the NQ peptides were changed according to circadian status of ZT00, ZT06, ZT12 and ZT18. Particularly, astrocytes synthesizing the NQ peptides which are determined by the present invention showed the highest fluorescence intensity at ZT06. In contrast, astrocytes showed relatively the lowest fluorescence intensity at ZT18 which is opposed to ZT06 with 12 hours. Although the fluorescence intensities at ZT00 and ZT12 were similar, they were higher than that of ZT18 and lower than that of ZT06. The changes of the fluorescence intensities according to circadian status were observed in all of the mature and premature forms of the NQ peptides. It was indirectly demonstrated that these two peptides are transcribed from the same gene and undergone post-translational modification.

It is showed that astrocytes synthesizing the NQ peptides react dynamically to circadian changes in the NQ peptide expressions. Therefore, it indicates that the NQ peptides are circadian peptides.

Example 11

Light-Dependent Secretion of the NO Peptide in Retina

According to the present embodiments, the NQ peptides were abundantly expressed in retina as well as SCN present in diencephalic hypothalamus of cerebral region (FIGS. 5, 6 and 8). Therefore, the NQ peptide expressions in retina are likely to relate to light-dependent regulation of SCN.

Therefore, in order to perform RIA (radioimmunoassay), the present inventors have carried out Chloramine-T assay to lable 125-Iodine to $9^{th}$ Tyr residue of the amino acid sequence of the NQ peptide which was as set forth in SEQ ID NO:2 and amidated at the carboxyl-terminus.

Figure 11:
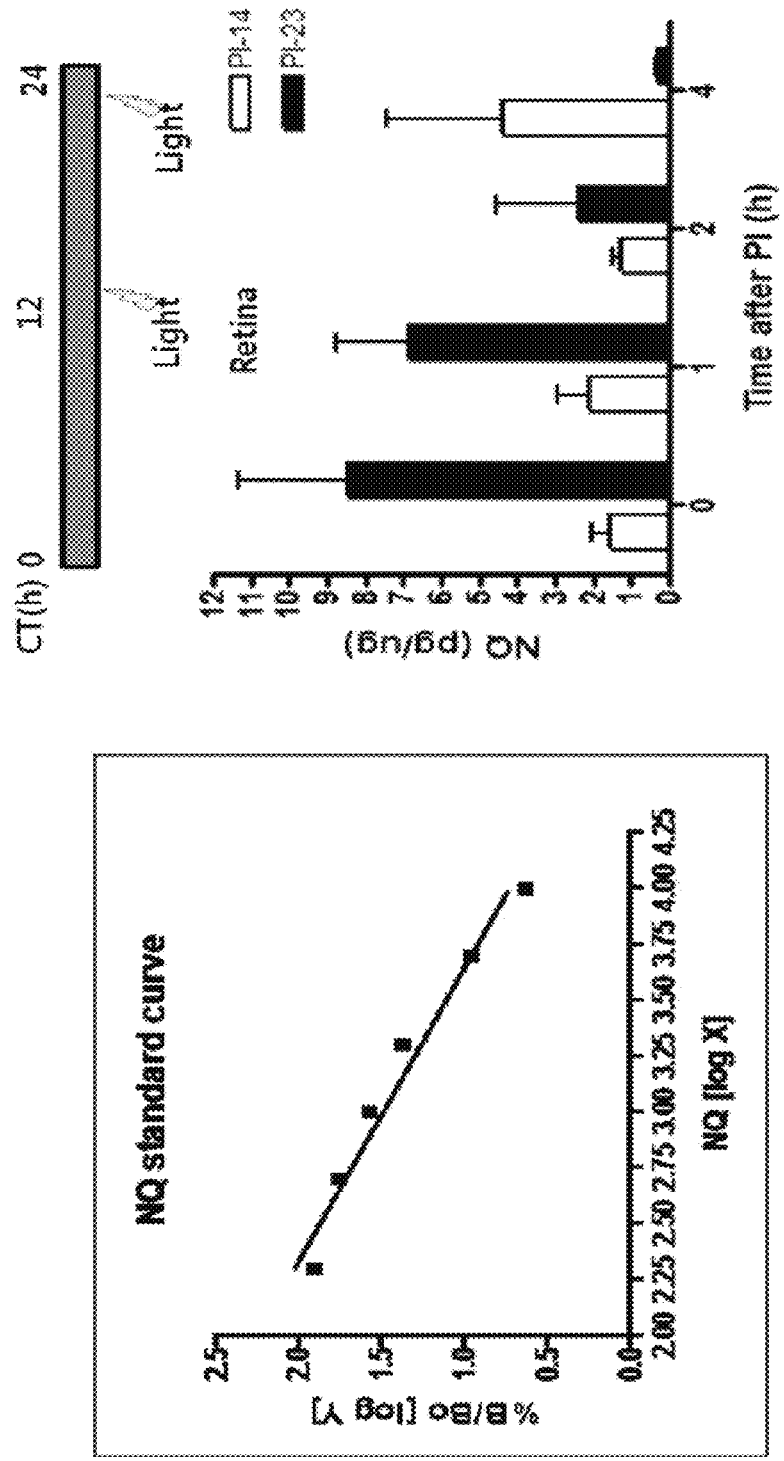
FIG. 11 is graphs showing the standard curve of the $^{125}$I-NQ peptide and the light-dependent NQ peptide expression level in retina using the standard curve. It shows that the expression was directly regulated by the strong external cue light.

The $^{125}$I-NQ peptide prepared thus was bound to the α-NQ-S antibody recognizing the epitope of SEQ ID NO:1 in Table 2 in competing with the synthetic NQ peptide having the amino acid of SEQ ID NO:2. It could be determined that the $^{125}$I-NQ peptide (Y-axis) bound to the α-NQ-S peptide antibody became lower with higher concentration of the NQ peptide (X-axis) (FIG. 11). Since a standard curve of the NQ peptide was constructed based on this, an absolute amount of the NQ peptide in mouse retina was calculated using the graph. This is described in more detail.

8-week-old wild type mice trained under 12:12 LD condition in which the light initiation was 09:00 and the light termination was 21:00 were adapted for 24 hours in dark. The mice were exposed to the light under different circadian statuses such as CT14 and CT23 to elucidate the light-dependent secretion of the NQ peptide according to circadian statuses. The mouse retina was isolated in dark at 0, 1, 2, and 4 hours after the light irradiation, and three mice were used for each status. The mice were sacrificed to obtain eyes. The pupil was holed with 26 G needle and the tissue was incised crosswise from the holed pupil to remove lens. To collect retina selectively, the melanin layer was removed through an optical microscope, and the retinal tissues were raked. The tissues were stored at −80° C. until use.

With increasing an amount of the NQ peptide as set forth in SEQ ID NO:2 in a certain amount of the $^{125}$I-NQ peptide (20,000 cpm), the competitive binding of the NQ peptide as set forth in SEQ ID NO:2 and the $^{125}$I-NQ peptide prepared by Chloramine-T assay to the α-NQ-S antibody was verified, and the amount of the NQ peptide contained in the sample through linear regression was distinguished. In the present experiment, normal rabbit serum was added to all reactions to distinguish CPM value by non-specific binding of the α-NQ-S antibody and to remove the present value in the actual calculation. As a result, it was shown that the $^{125}$I-NQ peptide bound to the α-NQ-S peptide antibody became lower with higher amount of the synthetic NQ peptide as set forth in SEQ ID NO:2 in a certain amount of the $^{125}$I-NQ peptide. Therefore, it could be determined that 2 types of the peptides to the same antibody bound competitively. In addition, statistical significances for the future and the absolute amount of the NQ peptide could be calculated by constructing linear regression curves (FIG. 11).

In order to analyze the amount of the NQ peptide present in the prepared sample, the certain amount of the $^{125}$I-NQ peptide and the sample (retinal protein) were added together to determine the competitive binding to the α-NQ-S antibody. The absolute amount of the NQ peptide contained in the retinal tissue was calculated by comparing the CPM value obtained through the present experiment with the standard curve obtained through the linear regression curve described above. As a result, the amounts of the present or consumed NQ peptides according to the light-exposed time in each circadian status could be determined. It may be interpreted that consumption of the NQ peptide synthesized in retina results from the secretion into SCN by responding to the light.

Therefore, although the NQ peptide is the light-dependent substance which is transmitted from retina to SCN, quantitative differences of the secretion may differ according to circadian status. It was based on that the amount of the NQ peptide in the CT14 was not significantly changed by the light, unlike that of the CT22.

Example 12

Analysis of Alterations of Circadian Expression Pattern of Biological Clock-Related Marker Gene Per2 by the NO Peptide Treatment The effects of the NQ peptides on periodicity of per2 in SCN were analyzed.

Animals used in this experiment were transgenic mice in which the construct inserted Luciferase gene behind per2 promoter was knocked-in. The mice were sacrificed. The brain was speedily isolated and sectioned in a thickness of 400 μm including SCN. The mouse brain tissue sections were incubated in media containing 1% penicillin/streptomycin antibiotics, 25% Horse Serum, 25% Hank's Buffered Salt Solution (HBSS), 50% Minimum Essential Medium (MEM) and 0.3 mM luciferin. At 5 days after the incubation, the synthetic NQ peptides were treated with 5 μM of final concentration. Then, luciferase activity derived from changes of per2 promoter activities was observed.

As a result, the luminescence activity of per2 promoter differently appeared depending on the time-courses of the NQ peptide treatments under circadian circumstances. For example, it could be observed that where the NQ peptides were treated at the point in which per2 shows the highest activity at 4 days after the incubation, the activity period of per2 promoter were not changed (approximately 24 hours). In contrast, it could be observed that where the NQ peptides were treated at the point in which per2 shows the lowest activity at 4 days after the incubation, the free-running period of per2 promoter were advanced by approximately 1 hour 30 min (to approximately 22.3 hours from approximately 24 hours). Accordingly, it was conclusive evidence that the NQ peptides may directly regulate circadian rhythms of mammals by regulating the per2 gene expression (FIG. 12).

Example 13

Phase-Dependent Drug Effects of the NQ Peptide in Per2

Drug effects of the NQ peptide according to changes of circadian phase of per2 were elucidated in the brain slide including SCN cultured by the method in Example 12. The present drug effects refer to changes of Per2 activity according to the NQ peptide treatment, and more specifically the phase advance of Per2.

The NQ peptides were treated with 100 nM of the concentration at 2, 6, 10, 14, 20 and 22 hours after the peak in Per2 activity with the 24-hour intervals wave. The treatment was maintained 4 hours. Then, the media were changed.

As a result, Per2 phase-advancing zone was toward advanced by the NQ peptide treatment by minimum 2 hours and maximum 4 hours (to approximately 18 hours from approximately 10 and 14 hours). Meanwhile, where the NQ peptides were treated at 2, 6 and 22 hours after the peak in Per2 activity, effects in the phase advance or the delay were negligible or barely shown. Therefore, it could be determined that the NQ peptide is the substance which directly affects circadian activity and it is the most effective substance at the lowest time zone in Per2 activity although the drug effects were differently shown according to circadian status (FIG. 13).

Example 14

Circadian Changes of Per2 Depending on NQ Peptide Dose

In order to validate drug effects with more specificity and accuracy of the NQ peptide regulating Per2 activity, the Per2-luc KI mouse brain sections including SCN were incubated as the same method in Example 12.

The NQ peptides were treated with 2 nM, 20 nM, 200 nM and 2000 nM of the concentrations for 4 hours to the sections at 10 hours after the peak in Per2 activity. Then, the media were changed to the original media (50% minimum essential medium, 25% gey's balanced salt solution, 25% horse serum, 36 mM glucose, and 100 units/ml aerosolized antibiotics) containing 0.3 mM luciferin to limit drug duration of the NQ peptide.

Vehicle was treated with 0.1% DMSO which solutionize the NQ peptides. Where the NQ peptides were treated, Per2 expression period was advanced proportionally to the concentration of the treated NQ peptides, particularly, 20-200 nM (FIG. 14). Therefore, it is interpreted that Per2 activity is changed in the NQ peptide dose-dependent manner and it greatly affects the phase advance rather than the phase delay.

Example 15

Analysis of Physiological Activities Using NO Peptide Mutants

As described in FIGS. 1 and 4, the mature form of the NQ peptide has the amino acid sequence as set forth in SEQ ID NO:2 and its carboxyl-terminus contained Gly was amidated. In addition, there are paralogs of the NQ peptide in several teleostei and amphibian. Therefore, validation of an important amino acid on the NQ peptide activity is very important.

To achieve this, the present inventors have synthesized mutants: deletion mutant sequencing from first Asn to tenth Leu among the amino acid sequences as set forth in SEQ ID NO:2; optical isomer mutant 1 in which the second Trp residue is modified to D-form Trp; and optical isomer mutant 2 in which the eleventh Lys residue is modified to D-form Lys.

The NQ peptide as set forth in SEQ ID NO:2 or 3, or the NQ peptide mutants were respectively treated to the incubated brain section including SCN. Particularly, the NQ peptide as set forth in SEQ ID NO:2 found in humans and mouse was simultaneously treated with the a-NQ-S antibody as neutralization substance to elucidate those specific effects with more accuracy. All forms of the NQ peptide as set forth in SEQ ID NO:2 found in humans and mouse, and the NQ peptide as set forth in SEQ ID NO:3 found in rat caused the advance effects in circadian activity. However, where the a-NQ-S antibody was simultaneously treated in order to neutralize, the effect was suppressed. In contrast, all various mutants did not cause the advance effects in circadian activity. Therefore, it could be understood that the carboxyl-terminus sequencing from the eleventh Lys residue to Gln as well as the second Trp residue and the eleventh Lys residue in the amino acid sequence of NQ peptide as set forth in SEQ ID NO:2 are very important in physiological activity.

Those skilled in the art will appreciate that the conceptions and specific embodiments disclosed in the foregoing description may be readily utilized as a basis for modifying or designing other embodiments for carrying out the same purposes of the present disclosure. Those skilled in the art will also appreciate that such equivalent embodiments do not depart from the spirit and scope of the disclosure as set forth in the appended claims.

What is claimed is:

1. A method for regulating circadian rhythm comprising: intravenously or subcutaneously administering to a mammalian subject in need thereof a composition comprising a peptide comprising the amino acid sequence as set forth in SEQ ID NO:2 in which the carboxyl group of the glutamine residue at the carboxyl-terminus is modified by an amino group.

2. The method according to claim 1, wherein the composition acts in suprachiasmatic nucleus (SCN) or habenula (Hb).

3. The method according to claim 1, wherein the composition acts in astrocytes.

4. A method for treating a circadian rhythm disorder comprising, intravenously or subcutaneously administering to a mammalian subject in need thereof a pharmaceutical composition comprising: (a) a therapeutically effective amount of a peptide comprising the amino acid sequence as set forth in SEQ ID NO:2 in which the carboxyl group of the glutamine residue at the carboxyl-terminus is modified by an amino group; and (b) a pharmaceutically acceptable carrier.

5. The method according to claim 4, wherein the circadian rhythm disorder is selected from the group consisting of jet lag syndrome, shift work sleep disorder, delayed sleep phase syndrome (DSPS), advanced sleep phase syndrome (ASPS), non-24-hour sleep-wake syndrome (non-24), irregular sleep-wake pattern, seasonal affective disorder (SAD), depression, bipolar disorder and insomnia by phase delay or phase advance.

6. The method according to claim 4, wherein the composition acts in suprachiasmatic nucleus (SCN) or habenula (Hb).

7. The method according to claim 4, wherein the composition acts in astrocytes.

* * * * *